(12) United States Patent
Robbins

(10) Patent No.: US 10,448,618 B2
(45) Date of Patent: Oct. 22, 2019

(54) SYSTEMS, METHODS AND APPARATUS FOR MONITORING ANIMAL HEALTH CONDITIONS

(71) Applicant: David S. Robbins, Garden City, KS (US)

(72) Inventor: David S. Robbins, Garden City, KS (US)

( * ) Notice: Subject to any disclaimer, the term of this patent is extended or adjusted under 35 U.S.C. 154(b) by 0 days.

(21) Appl. No.: 15/688,843

(22) Filed: Aug. 28, 2017

(65) Prior Publication Data

US 2019/0059337 A1   Feb. 28, 2019

(51) Int. Cl.
| | | |
|---|---|---|
| *G08B 23/00* | (2006.01) | |
| *A01K 29/00* | (2006.01) | |
| *A61B 5/00* | (2006.01) | |
| *G08B 25/08* | (2006.01) | |

(52) U.S. Cl.
CPC .......... *A01K 29/005* (2013.01); *A61B 5/0008* (2013.01); *A61B 5/0022* (2013.01); *G08B 25/08* (2013.01); *A61B 2560/06* (2013.01)

(58) Field of Classification Search
CPC .......................... A01K 29/005; G06F 19/3406
USPC ............................ 340/573.1, 573.4, 540, 541
See application file for complete search history.

(56) References Cited

U.S. PATENT DOCUMENTS

| | | | |
|---|---|---|---|
| 4,653,208 A | 3/1987 | Wassilieff | |
| 4,854,328 A | 8/1989 | Pollack | |
| 5,984,875 A | * 11/1999 | Brune | A01K 11/007 600/549 |
| 6,862,550 B1 | 3/2005 | Cook | |
| 7,196,628 B2 | 3/2007 | Hixson | |
| 9,848,577 B1 | 12/2017 | Brandao | |
| 2002/0010390 A1 | 1/2002 | Guice | |
| 2004/0044493 A1 | 3/2004 | Coulthard | |
| 2005/0241121 A1 | 11/2005 | Edland | |
| 2006/0163143 A1 | 7/2006 | Chirica | |
| 2006/0234209 A1 | 10/2006 | Walker | |
| 2008/0295529 A1 | 12/2008 | Kawaguchi | |
| 2009/0071413 A1 | 3/2009 | Stapelfeld | |
| 2009/0187392 A1* | 7/2009 | Riskey | A01K 11/007 703/11 |
| 2011/0106012 A1 | 5/2011 | Velarde | |

(Continued)

OTHER PUBLICATIONS

International Search Report and Written Opinion in International Application No. PCT/US2018/048198, dated Jan. 28, 2019.

(Continued)

*Primary Examiner* — Tai T Nguyen

(57) ABSTRACT

Embodiments disclosed herein include an intelligent health monitoring engine comprising: a processor; a memory; a communications interface to receive data from a remote intelligent health monitoring device; a non-transitory computer readable medium storing machine readable instructions that, when executed by the processor, cause the intelligent health monitoring engine to: acquire temperature data associated with an animal based on one or more temperature measures obtained by remote intelligent health monitoring device; determine whether the temperature data acquired satisfies a health condition criteria; identify a treatment modality to be delivered to the animal to treat a health condition if a health condition criteria has been satisfied; identify a caregiver for the animal; and provide treatment modality information to the caregiver.

20 Claims, 10 Drawing Sheets

(56) References Cited

U.S. PATENT DOCUMENTS

| | | |
|---|---|---|
| 2013/0247433 A1 | 9/2013 | Le Devehat |
| 2013/0292288 A1 | 11/2013 | Willes |
| 2014/0278327 A1 | 9/2014 | Hauenstein |
| 2014/0331942 A1 | 11/2014 | Sarazyn |
| 2015/0039239 A1 | 2/2015 | Shuler |
| 2015/0282457 A1 | 10/2015 | Yarden |
| 2016/0009482 A1 | 1/2016 | Martz |
| 2016/0015289 A1 | 1/2016 | Simon |
| 2016/0246934 A1* | 8/2016 | Dunlop .................. G16H 80/00 |
| 2017/0079247 A1 | 3/2017 | Womble |
| 2017/0156288 A1 | 6/2017 | Singh |
| 2018/0023828 A1 | 1/2018 | Lutz |

OTHER PUBLICATIONS

Tekvet Technologies Livestock Monitoring Systems Website, www.tekvet.com, as of Jul. 30, 2016.

\* cited by examiner

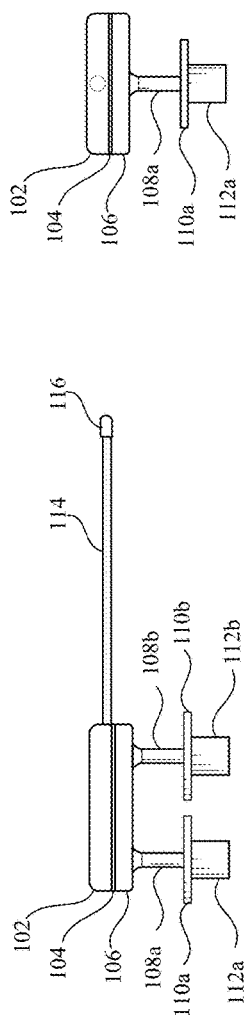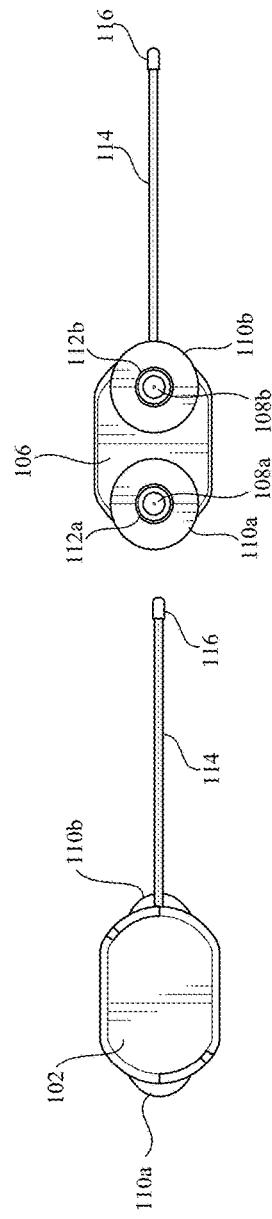

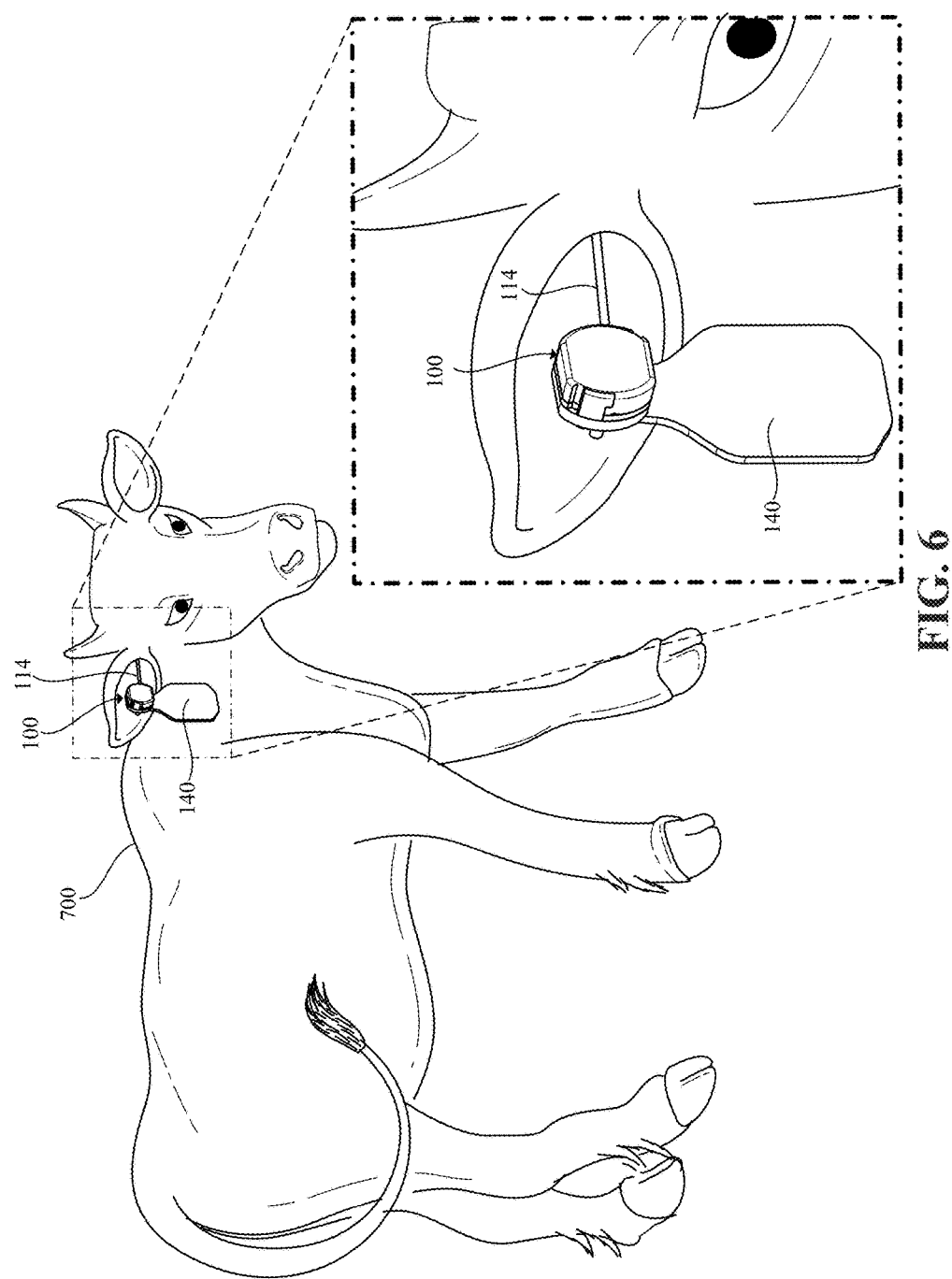

SYSTEMS, METHODS AND APPARATUS FOR MONITORING ANIMAL HEALTH CONDITIONS

TECHNICAL FIELD

The disclosed technology relates generally to animal healthcare, and more particularly some embodiments of the present disclosure relate to systems, methods and apparatus for monitoring animal health conditions.

BACKGROUND

Like humans, all animals are exposed to and experience a variety of disease, injury, illness, and other health conditions. People often provide care for animals, and wish to treat them upon learning of the onset of an illness or other health condition. Particularly for those whose livelihood depends on the survival of the animals they care for—e.g., farmers, ranchers, breeders, etc.—the health of animals under their care is of utmost concern. In many instances, to avoid certain diseases, caregivers may proactively vaccinate their animals to avoid serious illness and/or death that may occur if the animals are left unvaccinated. Such owners also often treat their herds with other drugs to help them combat various illnesses. This is especially common in the farming and ranching industries, where the longevity of animal's life directly correlate to the financial success of the farming or ranching operation. Because farmers and ranchers don't know which one or more animals in a given herd will come down with an illness, for example, they often treat their entire herd with the medications they would need to help them avoid the same. Such medications can be very expensive, directly affecting a farmer's profit margins.

The present disclosure, in accordance with one or more various embodiments, is directed toward enhanced technical solutions that inform owners (or others animal caregivers) about the health condition of their animals, on a real-time or near real-time basis, allowing the farmers to avoid having to treat an entire herd with a given medication, and instead only treat those animals that show signs of illness. The solutions disclosed herein, in accordance with one or more various embodiments, reduce animal fatalities, streamline diagnosis and treatment of animal illness, reduce the amount of medication or other drugs that animals (e.g., livestock) are exposed to throughout their lifetime, and save farmers and ranchers money throughout the lifespan of the animals in their herd. As detailed herein, embodiments of the present disclosure may include systems, methods and apparatus for intelligently monitor the health condition of animals, intelligently identify likely health conditions developing within a given animal based on various factors, and intelligently identify a treatment plan and solution for resolving the health condition.

BRIEF SUMMARY OF EMBODIMENTS

According to various embodiments of the disclosed technology, an intelligent health monitoring engine may include one or more of: a processor; a memory; a communications interface to receive data from a remote intelligent health monitoring device; a non-transitory computer readable medium storing machine readable instructions that, when executed by the processor, cause the intelligent health monitoring engine to: acquire temperature data associated with an animal based on one or more temperature measures obtained by remote intelligent health monitoring device; determine whether the temperature data acquired satisfies a health condition criteria; identify a treatment modality to be delivered to the animal to treat a health condition if a health condition criteria has been satisfied; identify a caregiver for the animal; and provide treatment modality information to the caregiver.

In some embodiments, the remote intelligent health monitoring device is attached to the ear of the animal, and the temperature data is based on heat sensed within the ear canal of the animal. In some embodiments, the health condition criteria comprises a temperature threshold. In some embodiments, determining whether temperature data satisfies a health condition criteria is based upon one or more of the ambient temperature near the animal's location, the length of time during which the temperature data satisfied the health condition criteria.

In some embodiments, identifying a treatment modality to be delivered to the animal to treat a health condition is based on one or more of: the animal's breed, age, size, treatment history, and known allergies. In some embodiments, identifying a treatment modality to be delivered to the animal to treat a health condition is based on one or more of: the treatment's availability, effectiveness, and cost.

In some embodiments, identifying a treatment modality to be delivered to the animal to treat a health condition comprises selecting among a plurality of medications to deliver to the animal.

In some embodiments, providing treatment modality information to the caregiver comprises: generating one or more of a text message, an email, or a phone call describing the treatment modality information. In some embodiments, treatment modality information comprises one or more of: a medication type, availability, dosage, and delivery site.

According to various embodiments of the disclosed technology, an intelligent health monitoring engine may include one or more of: a processor; a memory; a communications interface to receive data from a remote intelligent health monitoring device; a non-transitory computer readable medium storing machine readable instructions that, when executed by the processor, cause the intelligent health monitoring engine to: acquire temperature data associated with an animal based on one or more temperature measures obtained by remote intelligent health monitoring device; determine whether temperature data satisfies a health condition criteria; identify a treatment modality to be delivered to the animal to treat a health condition if a health condition criteria has been satisfied; identify a caregiver for the animal; provide treatment modality information to the caregiver.

In some embodiments, the remote intelligent health monitoring device is attached to the ear of the animal, and the temperature data is based on heat sensed within the ear canal of the animal.

In some embodiments, the health condition criteria comprises a temperature threshold.

In some embodiments, determining whether temperature data satisfies a health condition criteria is based upon one or more of the ambient temperature near the animal's location, the length of time during which the temperature data satisfied the health condition criteria.

In some embodiments, identifying a treatment modality to be delivered to the animal to treat a health condition is based on one or more of: the animal's breed, age, size, treatment history, and known allergies. In some embodiments, identifying a treatment modality to be delivered to the animal to treat a health condition is based on one or more of: the treatment's availability, effectiveness, and cost.

In some embodiments, identifying a treatment modality to be delivered to the animal to treat a health condition comprises selecting among a plurality of medications to deliver to the animal.

In some embodiments, providing treatment modality information to the caregiver comprises: generating one or more of a text message, an email, or a phone call describing the treatment modality information. In some embodiments, treatment modality information comprises one or more of: a medication type, availability, dosage, and delivery site.

According to various embodiments of the disclosed technology, an intelligent health monitoring engine may include one or more of: a processor; a memory; a communications interface to receive data from a remote intelligent health monitoring device; a non-transitory computer readable medium storing machine readable instructions that, when executed by the processor, cause the intelligent health monitoring engine to: acquire physical parameter data associated with an animal based on one or more physical parameter measures obtained by remote intelligent health monitoring device; determine whether the physical parameter data satisfies a health condition criteria; identify a treatment modality to be delivered to the animal to treat a health condition if a health condition criteria has been satisfied; identify a caregiver for the animal; provide treatment modality information to the caregiver.

According to various embodiments of the disclosed technology, an intelligent health monitoring device may include one or more of: a housing including a casing member releasably couplable with a base member, wherein the casing member and the base member create an internal cavity when in a coupled configuration; an environment resistant seal disposed between the casing member and the base member, wherein the environment resistant seal is held between the casing member and the base member when the casing member and the base member are in the coupled configuration; one or more studs coupled to a side of the base member, the studs configured to pierce biological tissue; a circuit configured to support electrical connections, the circuit supporting electrical connections between at least a processing engine, a memory, a transmitter, and a power source; wherein the processing engine, memory, transmitter circuit, and power source are operatively coupled together and held within the internal cavity; a conductor operatively coupled to the circuit and a heat sensor, a portion of the conductor disposed within a flexible cord passing through an opening in the housing and extending outside the internal cavity to at least a portion of the heat sensor.

In some embodiments, intelligent health monitoring devices of the present disclosure may include a heat sensor in the form of a thermistor. In some embodiments, the heat sensor is a thermistor having a resolution of less than 3 degrees Fahrenheit.

In some embodiments of the intelligent health monitoring device of the present disclosure, the flexible cord and the heat sensor may be configured to be at least partially disposed within an anatomical orifice of an animal. For example, in some embodiments of the intelligent health monitoring device of the present disclosure, flexible cord and the heat sensor are configured to be at least partially disposed within an ear canal of an animal.

In some embodiments of the intelligent health monitoring device of the present disclosure, the transmitter may be a component member of communications interface circuit. The communications interface circuit may include one or more of a Zigbee compliant communications module, a Bluetooth compliant communications module, a Wi-Fi compliant communications module, and a cellular communications module. In some embodiments of the intelligent health monitoring device, the communications interface circuit can transmit an electromagnetic signal to a remote receiver located over 1000 feet from the intelligent health monitoring device. In some embodiments of the intelligent health monitoring device, the communications interface circuit can transmit an electromagnetic signal through the air to a remote receiver located up to 1500 feet away from the intelligent health monitoring device in any direction.

In some embodiments of the intelligent health monitoring device of the present disclosure, the one or more studs are formed from a rigid material. In some embodiments, the one or more studs are formed from a rigid material that is biocompatible. In some embodiments, the one or more studs include a shaft and a head, the head being pointed so as to be adapted for piercing the biological tissue of an animal.

In some embodiments of the intelligent health monitoring device of the present disclosure, the environment resistant seal is made of a compressible, non-rigid material. In some embodiments, at least a portion of the environment resistant seal comprises one of a thermoplastic elastomer and a thermoset rubber. In some embodiments, at least a portion of the environment resistant seal comprises santoprene.

In some embodiments of the intelligent health monitoring device of the present disclosure, the largest dimension of the base member is less than 3 inches. In some embodiments, the largest dimension of the base member is about between 1.5 and 1.7 inches.

In some embodiments of the intelligent health monitoring device of the present disclosure, the weight of the HMD is less than 33 grams. In some embodiments, the weight of the HMD is between 20 and 30 grams. In some embodiments the weight of the HMD may be greater than or less than 20 grams.

Some embodiments of the intelligent health monitoring device of the present disclosure further comprise one or more of a light source configured to emit light responsive to a signal received from a remote source, and an audio source configured to emit sound responsive to a signal received from a remote source.

In some embodiments of the intelligent health monitoring device of the present disclosure, the power source is one of a rechargeable power source, a removable power source, and a solar power source.

According to various embodiments of the disclosed technology, an intelligent health monitoring device may include one or more of: a casing member releasably couplable with a base member, wherein the casing member and the base member create an enclosure having a single opening when in a coupled configuration; an environment resistant seal disposed between the casing member and the base member, wherein the environment resistant seal is held between the casing member and the base member when the casing member and the base member are in the coupled configuration; one or more studs coupled to a side of the base member and extending at least 5 millimeters from the side of the base member, the studs configured to pierce biological tissue; a circuit held within the enclosure, the circuit comprising: a processing engine, a memory, a transmitter, and a power source, wherein the processing engine, memory, transmitter, and power source are operatively coupled together and held within the enclosure; a conductor operatively coupled to the circuit and a heat sensor, the conductor passing through the opening of the enclosure and leading to at least a portion of the heat sensor held outside the enclosure; and a sleeve coupled to the casing member and surrounding the conductor between the casing member and the portion of the heat sensor held outside the enclosure.

According to various embodiments of the disclosed technology, an intelligent health monitoring device may include one or more of: a casing member releasably couplable with a base member, wherein the casing member and the base member create an enclosure having one or more openings when in a coupled configuration; a moisture resistant seal held between the casing member and the base member when the casing member and the base member are in the coupled configuration; one or more studs coupled to a side of the base member, the studs configured to pierce biological tissue; a circuit held within the enclosure, the circuit including one or more of a processing engine, a memory, a transceiver, and a battery; wherein the processing engine, memory, transceiver, and battery are operatively coupled together and releasably held within the enclosure; and a cord coupled with the circuit one end, the cord including an insulation sleeve surrounding one or more conducting wires, the conducting wires connected to a heat sensor held outside the enclosure.

Some embodiments of the present disclosure include a method for monitoring the health of an animal by obtaining real-time temperature measurements acquired by an intelligent health monitoring device. In accordance with some embodiments, the method includes one or more of the following steps: attaching an intelligent health monitoring device to the ear (or other body part) of an animal; causing the intelligent health monitoring device to obtain a temperature measurement data associated with the animal (e.g., the temperature within the animal's ear canal); transmitting the temperature measurement data from the intelligent health monitoring device to a receiver; receiving at the receiver the temperature measurement data transmitted from the intelligent health monitoring device. In some such embodiments, the intelligent health monitoring device comprises: a casing member releasably couplable with a base member, wherein the casing member and the base member create an enclosure having one or more openings when in a coupled configuration; a moisture resistant seal held between the casing member and the base member when the casing member and the base member are in the coupled configuration; one or more studs coupled to a side of the base member, the studs configured to pierce biological tissue; a circuit held within the enclosure, the circuit comprising a processing engine, a memory, a transceiver, and a battery; wherein the processing engine, memory, transceiver, and battery are operatively coupled together and releasably held within the enclosure; and a cord coupled with the circuit one end, the cord comprising a sleeve surrounding one or more conducting wires, the conducting wires connected to a heat sensor held outside the enclosure.

Other features and aspects of the disclosed technology will become apparent from the following detailed description, taken in conjunction with the accompanying drawings, which illustrate, by way of example, the features in accordance with embodiments of the disclosed technology. The summary is not intended to limit the scope of any inventions described herein, which are defined solely by the claims attached hereto.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

Some of the figures included herein illustrate various embodiments of the disclosed technology from different viewing angles. Although the accompanying descriptive text may refer to such views as "top," "front," "back," "bottom" or "side" views, such references are merely descriptive and do not imply or require that the disclosed technology be implemented or used in a particular spatial orientation unless explicitly stated otherwise.

FIG. 2A illustrates a side view of an example intelligent animal health monitoring device (hereinafter, referred to as an "HMD") in accordance with one or more embodiments of the present disclosure.

FIG. 2B illustrates a rear side of an example HMD in accordance with one or more embodiments of the present disclosure.

FIG. 2C illustrates a top view of an example HMD in accordance with one or more embodiments of the present disclosure.

FIG. 2D illustrates a bottom view of an example HMD in accordance with one or more embodiments of the present disclosure.

FIG. 6 illustrates an example HMD attached to an animal, in this depiction attached to an ear of a cow in accordance with one or more embodiments of the present disclosure.

The figures are not intended to be exhaustive or to limit the disclosed technology to the precise form disclosed. It should be understood that the invention can be practiced with modification and alteration, and that the disclosed technology be limited only by the claims and the equivalents thereof.

DETAILED DESCRIPTION OF THE EMBODIMENTS

Embodiments of the present disclosure enable animal caregivers to more precisely and intelligently monitor the health of the animals they care for, and to more effectively and efficiently treat animals that exhibit one or more symptoms of a developing (or already developed) health condition. The systems, methods, and apparatus for realizing the various benefits of the presently disclosed technology may be tailored to the individual needs of a given animal caregiver's operation, on the basis of the factors of greatest import. Several example implementations of the present technology are discussed within this disclosure, it being understood that these example implementations are in no way intended to limit the robust features that the present disclosure teaches, suggests, or otherwise enables. Rather, the example implementations disclosed herein are intended to illustrate various utility of the present technology, and are further intended to assist the reader and provide clarity and enhanced understanding of the technology disclosed herein.

Figure 1:
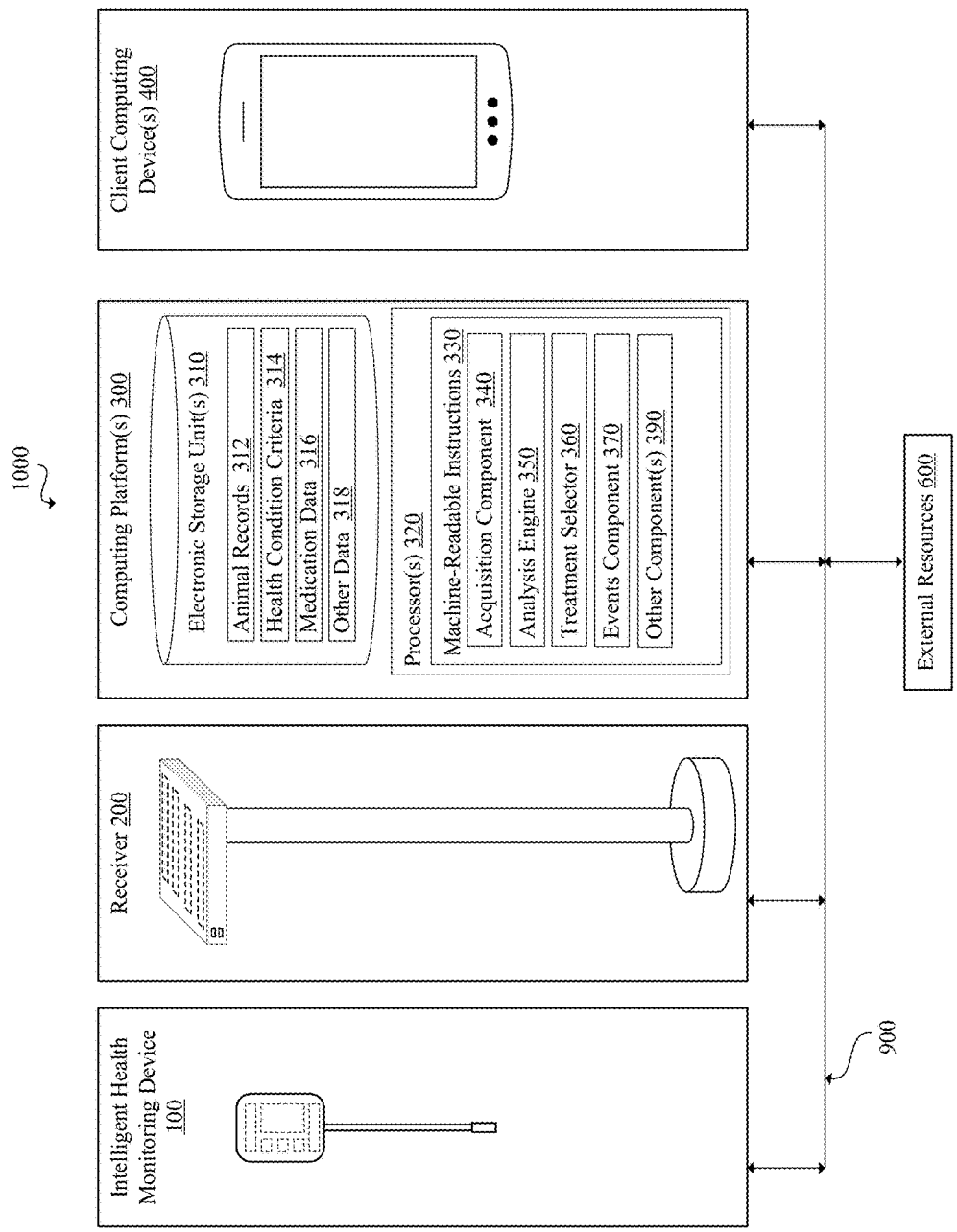
FIG. 1 illustrates a block diagram representing one or more elements of an example system for monitoring animal health condition in accordance with one or more embodiments of the present disclosure.

FIG. 1 illustrates a block diagram representing one or more elements of an example system for monitoring animal health condition in accordance with one or more embodiments of the present disclosure. As shown, system 1000 may include one or more HMDs 100 (intelligent animal health monitoring devices), one or more receivers 200, one or more computing platforms 300, and one or more client devices 400.

HMD 100 is attachable to the body of an animal, and includes hardware and software (described in more detail below) that senses physical parameters associated with the animal, and in some embodiments with the animal's environment, and transmits signals representative of the same to one or more of receivers 200 (e.g., receivers 200 within range of the HMD's transmission). The one or more receivers 200 decode the signals received from the one or more HMDs 100 to obtain the data represented thereby, and provide the data to one or more computing platforms 300. The one or more computing platform 300s may receive the data (or signals representing the data) from the one or more receivers 200 for storage, and to perform analysis or further operations thereon. In some embodiments, computing platform uses the data obtained from receivers 200 to detect the onset of a developing (or already developed) health condition in a given animal, and determine an appropriate treatment modality for the given animal based on information available to system 1000. In some embodiments, if the one or more computing modules 300 determine that a particular treatment is appropriate or recommended for a given animal based on the information available to the system 1000, the one or more computing modules 300 may provide information to (or make such information accessible by) one or more client devices 400 (e.g., remote desktop computers, smartphones, tablets, etc.).

As symbolically shown in FIG. 1, any one or more of the elements in the system may communicate with, or be accessible to, any of the other elements for sub elements within system 1000. As shown, such communication may take place over one or more communication links 900. Communications links 900 may be provided via any communications interface desired, whether wired or wireless, including any such communications interface (and associated hardware, software, protocols, etc.) already known in the art, as well as any later developed communication interface technology later developed. It should further be understood that some embodiments of the present disclosure may not include each element depicted in FIG. 1. Because various elements within system 1000 are equipped with one or more communications interfaces, one or more for all such elements main access various external resources over a communications link, the various external resources (e.g., external databases accessible over the Internet) providing additional information and functionality that provides further enhancements to embodiments of the technology disclosed herein, as described in detailed examples below. In various embodiments of the elements depicted in FIG. 1 will now be discussed in more detail.

FIGS. 2A-2D illustrate various views of an example HMD in accordance with one or more embodiments of the present disclosure. FIG. 2A illustrates a side view of an example HMD in accordance with one or more embodiments of the present disclosure. FIG. 2B illustrates a rear side of an example HMD in accordance with one or more embodiments of the present disclosure. FIG. 2C illustrates a top view of an example HMD in accordance with one or more embodiments of the present disclosure. FIG. 2D illustrates a bottom view of an example HMD in accordance with one or more embodiments of the present disclosure. As these figures depict the same example HMD embodiment, they will be discussed together with like numerals referring to like elements of the example HMD embodiment.

As shown in FIGS. 2A-2D, HMD 100 may include a housing including a casing member 102 (sometimes referred to herein as a first member) releasably coupled with a base member 106 (sometimes referred to herein as a second member). When coupled together, casing member 102 and base member 102 may define an internal cavity wherein electronic components may be disposed. Environment resistant seal 104 may be disposed between at least a portion of casing member 102 and at least a portion of base member 106 to provide at least partial protection from environmental elements to interior components held inside the interior of the housing of HMD 100—e.g., to inhibit dust, water, and other particulates of the external environment from entering the internal cavity area of the HMD 100 housing.

HMD 100 may include one or more studs 108 to provide an attachment mechanism to install the HMD 100 onto the body of an animal. HMD may further include one or more fittings 110 that provide a releasable couple with the one or more studs 108. In some embodiments, fittings 110 may including a cap 112 that may protect or otherwise guard the distal end of the studs (which may in some embodiments be pointed/sharpened). In some embodiments, one or more studs 108 may include a sharpened portion adapted to pierce through the surface of an animal's skin to realize the attachment. That is, the one or more studs 108 may be sharpened at a distal end (i.e. the end opposite the end that is coupled to the base member 106) so that an operator may pierce the ear (or other surface) of an animal to attach the HMD 100 to the body of the animal, for example.

To avoid deformations of the studs 108 over time (e.g., by bending inward or outward with extended use), strong materials may be used to form the rod or shaft of the studs 108. For example, some non-limiting embodiments may include a rigid nylon ABS blend. In still further embodiments, the structure of the studs may be configured to avoid bending. For instance, the diameter (or largest cross-sectional dimension, if not annular) of the studs may be between 2 and 10 millimeters.

As shown in FIGS. 2A-2D, HMD 100 may include a thermistor 116 (or other sensor type, as desired for the given application) disposed at the end of a flexible cord 114 that extends outside the interior cavity of the HMD 100. In some embodiments, thermistor 116 is connected to electronic componentry held in the interior cavity of HMD 100 such that the temperature readings detected by thermistor 116 may be communicated to (e.g., via an electric signal generated as the sensor transduces the physical parameter it detected), processed by, stored upon, and/or transmitted by HMD 100. In some embodiments, as shown, the connection between thermistor 116 and the electronic componentry held in the interior cavity of the HMD 100 housing is provided by a wire within cord 114 that traverses through a side wall of either or both the casing member 102 and the base member 106 and ties into the aforementioned electronic componentry. In some embodiments, the length that the flexible cord 114 extends outside the housing of the HMD is adjustable. Example electronic componentry will be discussed in more detail with reference to FIG. 5, which may be utilized in one or more embodiments.

Referring still to FIGS. 2A-2D, though HMD 100 is depicted in this example embodiment to be equipped with a thermistor 116, one or skill in the art should appreciate that HMD 100 may be equipped with any one or more sensors adapted to detect any one or more physical parameters about the animal to which the HMD 100 is associated, or about the environment within which said animal is located. It should be further understood that such sensors may be disposed in the interior cavity of the HMD 100, outside of the interior cavity of the HMD 100, and in some instances may be partially disposed outside the interior cavity of the HMD 100, and partially disposed outside the interior cavity of the HMD. In some such embodiments the portion of the sensor device disposed partially outside the interior cavity of the HMD 100 may be connected, via a wired or wireless connection, with the complementary portion of the sensor device disposed within the interior cavity of the HMD 100.

With reference to the environment resistant seal 104, such may provide at least some protection from environmental elements to the interior components held inside the interior of the housing of HMD 100. In some embodiments, environment resistant seal 104 provides a substantially waterproof seal along an edge of a side wall of the casing member 102. In some embodiments, environment resistant seal 104 provides a substantially waterproof seal along an edge of a side wall of the base member 106. In some embodiments, at least a portion of the environment resistant seal 104 is a soft or flexible material (e.g., sanoprene) that is subject to compression upon incident compressive forces. In some embodiments a portion of the environment resistant seal 104 may be pinched (and consequently compressed) between the casing member 102 and base member 106 as casing member 102 and base member 106 are brought together and releasably coupled together.

With reference to the releasable couple feature noted previously, the releasable couple may be provided using any mechanism, including any known in the art and any later developed. Such releasable couple provides operators with quick and easy access the internal electronic components (discussed in more detail below). Releasable couples may be used to enable operators to quickly and easily take apart individual pieces of the HMD 100 for repair, replacement, or otherwise. Indeed, in some embodiments it may be desirable to separate one part of the HMD 100 from another part of the HMD 100 for a time, and also to have the ability to recouple said parts back together at a later time. Some examples of such releasable couple mechanisms may include snap-fit (e.g., torsional, cantilever, annular, etc.), twist-fit (e.g., threaded), pressurized (e.g., adjustable valve regulated hermetic seal).

For example, if an HMD 100 is discovered to be malfunctioning, an operator may wish to remove the casing member 102 (containing the damaged electronic components, for example) from the base member 106 (which may be pierced through the animal's ear, for example), so that the operator can obtain with very little effort (by simply uncoupling the casing member 102 from the base member 106, for example) the pieces he/she needs to refurbish, replace, or clean to repair the HMD 100.

As suggested above, such releasable couple mechanisms may be deployed between any one or more of the hardware elements of HMD 100 (in addition to the casing member 102 and the base member 106 discussed above) to provide the ability to quickly and easily separate one part of the HMD 100 from another 100. Taking the example in the previous paragraph a step further, the HMD 100 may include electronic componentry tied into a circuit, e.g., a printed circuit board ("PCB"), adapted to be held within a cavity region of the casing member 102 of the HMD 100 housing. For ease of description throughout this disclosure, any electronic circuit boards, including printed circuit boards, integrated circuits, or other circuit arrangements/formats, will generally be referred to herein as PCBs, it being understood that in some embodiments the circuitry deployed therein is does not take the form of a printed circuit board. With that understanding, an example PCB itself may be releasably coupled to an interior wall of the casing member 102 so that the PCB may be securely positioned when coupled. Thus, an operator may uncouple the casing member 102 from the base member 106 to get at the PCB, then further uncouple the PCB from the casing member 102 by disengaging the releasable couple mechanism such that the PCB may be removed from the interior wall of the casing member 102. In some such instances, once the PCB is removed, the operator may wish to recouple the casing member 102 of the HMD 100 with the base member 102 so as to keep the parts together until the repaired PCB is ready to be reinstalled (i.e., recoupled with the casing member 102) for further operation within system 1000.

As shown in FIGS. 2A-2D, HMD 100 may include a cord 114 connecting the thermistor 114 to the housing of the HMD 100 (and the electronic componentry held therein). In some embodiments, the cord is made of a non-rigid (i.e., substantially flexible) material such as a medical grade polymer material. The cord 114 may in some embodiments be a sleeve (e.g., a tubular structure) that covers wiring between the thermistor and the housing of the HMD 100. The cord 114 may in some embodiments be a sleeve that covers wiring between the thermistor and the housing of the HMD 100, and in some embodiments the sleeve styled cord 114 may also include a closed distal end, the thermistor (or other sensor) being enclosed entirely within the cord 114 such that is not exposed to the external elements of the surrounding environment. The cord may be provided with a length and width appropriate to guide (and in some instanced hold) the thermistor 116 to the proper location on the animal to obtain the desired reading. For example, if the temperature within the ear canal of an adult cow of a particular size is the desired measure sought by the operator, the cord 114 may be about between 2-4 inches in length, and less than ¼ inch in diameter (or other width dimension depending on the cross-sectional profile of the cord) such that HMD 100 may installed onto the adult cow's ear (e.g., with studs 108a and 108b piercing through the cow's ear in a location on the ear such that the cord 114 may be guided into and remain disposed within the ear canal of the cow to obtain the desired temperature reading. The foregoing is a specific and non-limiting example, and one of skill in the art will appreciate that the embodiments described herein may be modified in various manners (e.g., different sensors, different HMD attachment locations, etc.) without departing from the scope and spirit of the present disclosure.

Figure 3:
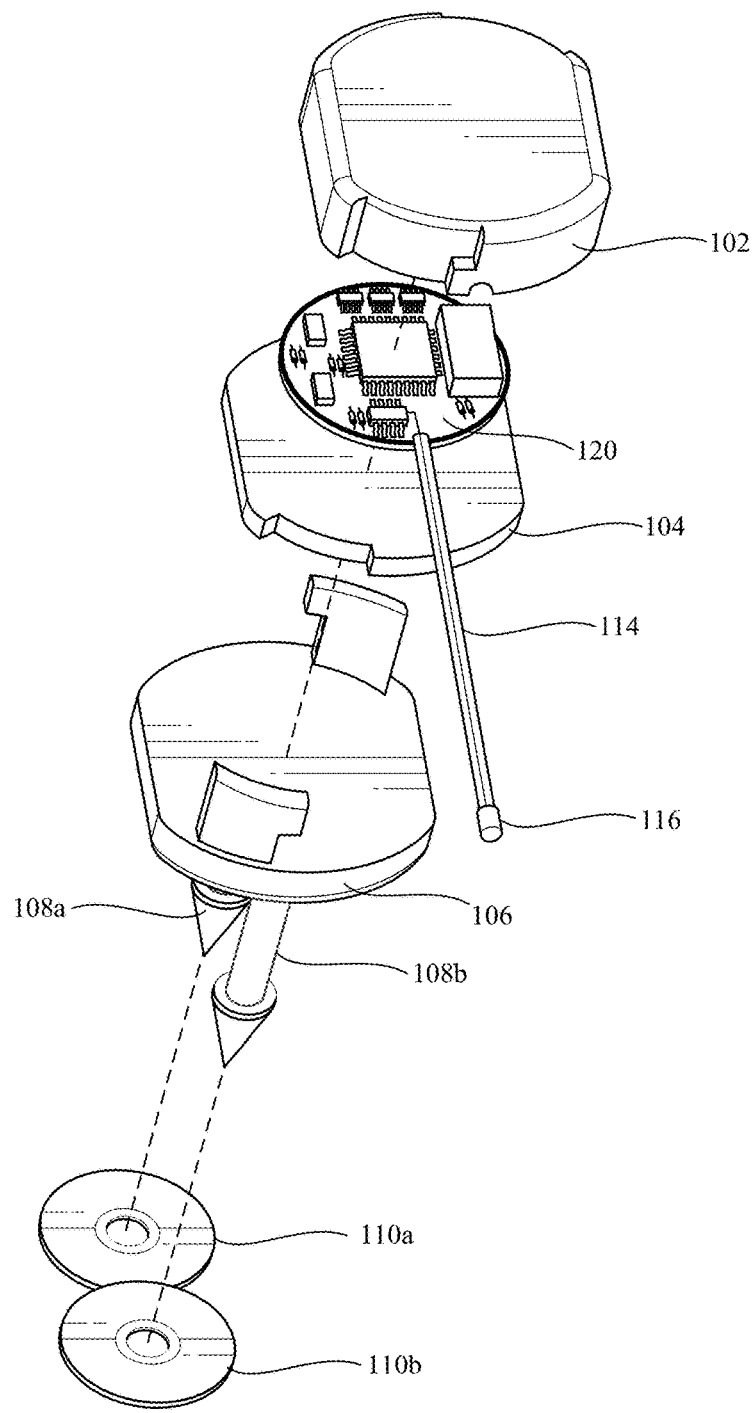
FIG. 3 illustrates an exploded perspective view of an example HMD in accordance with one or more embodiments of the present disclosure.

FIG. 3 illustrates an exploded perspective view of another example HMD 100 in accordance with one or more embodiments of the present disclosure. As shown, HMD 100 may include a casing member 102 defining at least a portion of a cavity within which an electronic circuit board 120 may be at least partially disposed. HMD 100 may also include an environment resistant seal 104 to provide at least partial protection from environmental elements to interior components held inside the interior of the housing of HMD 100—e.g., to inhibit dust, water, and other particulates of the external environment from entering the internal cavity area of the HMD 100 housing. In the example embodiment shown in FIG. 3, environment resistant seal 104 is notched to accommodate the releasable coupling features that enable casing member 102 and base member 106 to be releasably coupled together. Also in the example embodiment shown, environment resistant seal 104 is configured to cover or otherwise overlay the cavity created by the structure of casing member 102, thereby spanning from edge-to-edge of the casing member 102 and creating a layer or barrier between casing member 102 and base member 106. Though neither of the foregoing features need be present in embodiments of the presently disclosed technology, in some instances they may be present.

As shown, base member includes or is otherwise coupled with two studs 108, namely stud 108a and stud 108b. Studs 108 may be formed as rods coupled to and extending outward from the base member 106. Rods may have sharp or pointed heads (e.g., conical shaped heads, as shown in FIG. 3) that create a lip or shelf designed to prevent a pierced surface from slipping off the stud without considerable force (e.g., intentional force). As shown, the lip is formed by the base of the conical heads of the studs 108, the base of the conical heads extending radially outward from the rod structure of studs 108, the lip arising on account of the conical base having a diameter larger than the diameter (or other cross sectional width dimension depending on the cross-sectional profile of the stud) of at least a portion of the rod structure (a.k.a. the shaft) of studs 108. In some embodiments, the lip or shelf can reduce the chance of, or even prevent, a pierced surface from slipping off the stud without considerable force.

Figure 4:
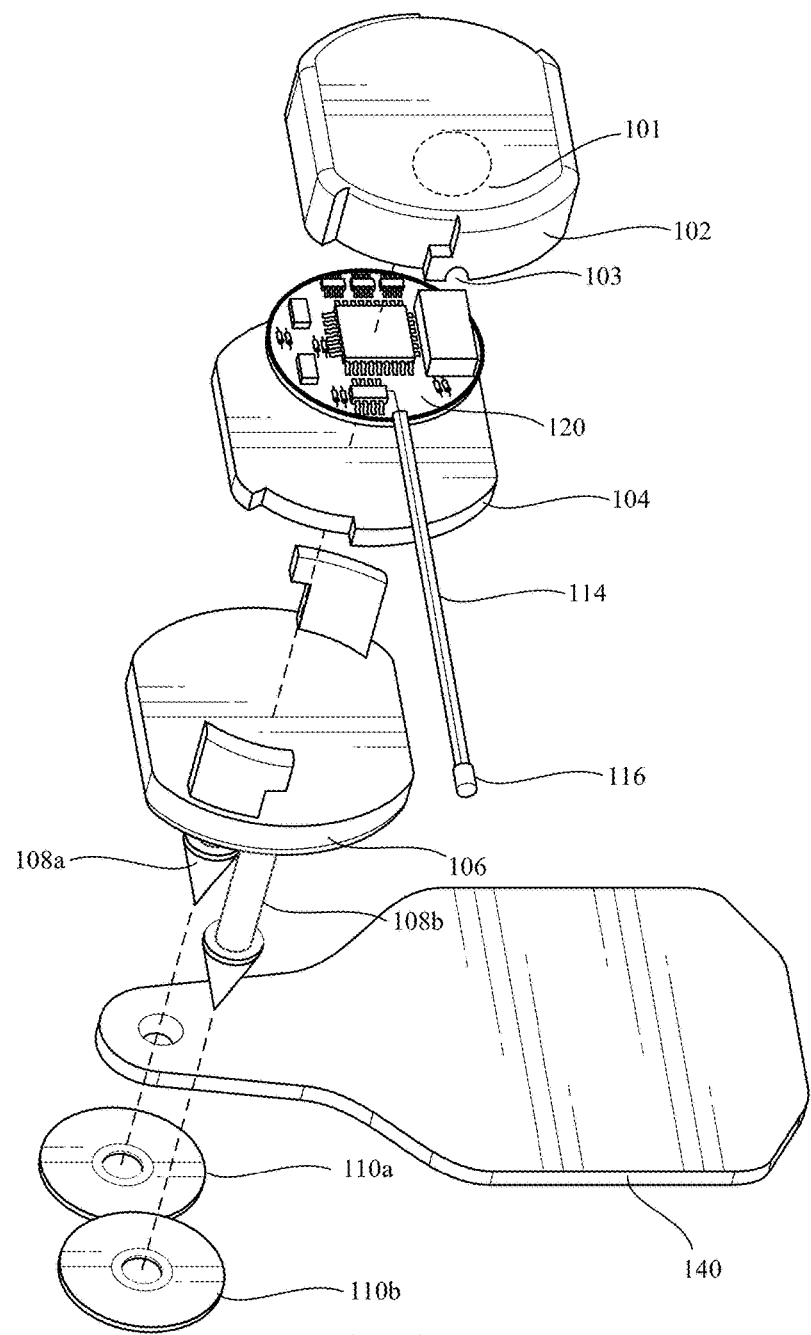
FIG. 4 illustrates an exploded perspective view of another example HMD in accordance with one or more embodiments of the present disclosure.

Though depicted with a lip or shelf structure in FIG. 3, some embodiments may be implemented without such a feature. Indeed, in some embodiments, studs 108 may simply comprise a shaft with a flat distal end. In other embodiments studs 108 may include a feature designed for complementary releasable coupling with a fitting. And in still further embodiments, studs 108 may be implemented with a combination of anyone or more of the foregoing. For example, as shown, the HMD 100 may include studs 108 that are both sharp at a distal end, shelved or lipped, and also fitted for releasable coupling with one or more complementary fittings 110, namely fitting 110a and fitting 110b as shown in FIG. 3. Fittings 110 may serve to further reduce the chance of, or further ensure the prevention of, a pierced surface from slipping off the stud without considerable force. Such fittings may be particularly useful when operators desire to secure other items to HMD 100 via one or more of studs 108, such as an ear tag identifier 140 as shown in FIG. 4. In alternative embodiments, the tag identifier 140 itself may be configured with a structure (e.g., an opening and suitable material) similar to a fitting 110 such that the ear tag identifier 140 may serve as both the fitting and as well as the identifier (foregoing the need for fitting 110a in FIG. 4, in some embodiments.

FIG. 4 illustrates an exploded perspective view of another example HMD 100 in accordance with one or more embodiments of the present disclosure, here depicted with an ear tag identifier 140 having a hole through which one or more of studs 108 may pass. This way, studs 108 of HMD 100 can be used as a mechanism to attach other items (e.g., an ear tag identifier 140) that may aid an operator in maintaining an organized operation.

In addition to the ear tag identifier 140, the embodiment in FIG. 4 is different from the embodiment shown in FIG. 3 in other ways. As shown, HMD 100 may include a light source 101 (e.g. an LED, a laser beam generator, or other light source). The light source may be configured to emit light, which may pass through one or more openings, apertures, or windows (e.g., covered by glass, plastic, or otherwise) to provide one or more visual indications to the operator. For instance, suppose an operator has a herd of 975 cattle roaming in a field, and system 1000 has notified him that cow number 702 has developed a particular health condition and needs a particular antibiotic. System 1000 may automatically, or upon request by an end user (such as the operator, handler, etc.) cause the light source 101 of cow number 702's HMD 100 to flash a red light, for example. This way, especially in the evening hours or in dark quarters, the operator may more easily locate cow number 702 among the herd as they are roaming in the field. In some embodiments the light parameters (e.g., frequency, wavelength, intensity, and emission pattern or color) may be adjustable or set by default.

In still further embodiments, HMD 100 may include an audio source (e.g. a speaker). The audio source may be configured to emit sound, which may in some instances be heard outside the exterior of HMD 100's housing to provide one or more audible indications to the operator. For instance, extending the example above where an operator has a herd of 975 cattle roaming in a field, and system 1000 has notified him that cow number 702 has developed a particular health condition and needs a particular antibiotic. System 1000 may automatically, or upon request by an end user (such as the operator, handler, etc.) cause the audio source of cow number 702's HMD 100 to beep periodically, for example. This way, especially in the evening hours or in dark quarters, the operator may more easily locate cow number 702 among the herd as they are roaming in the field. In some embodiments the audio parameters (e.g., frequency, volume, pitch, and emission pattern) may be adjustable or set by default.

Figure 5:
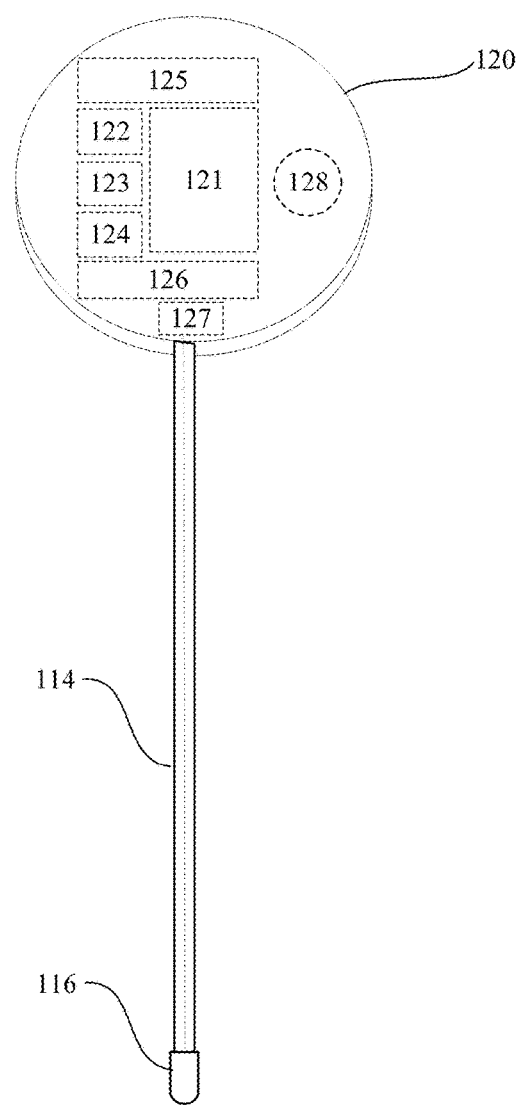
FIG. 5 illustrates a block diagram representing various electronic components of an example HMD in accordance with one or more embodiments of the present disclosure.

FIG. 5 illustrates a block diagram representing various electronic components that may be implemented in an example HMD in accordance with one or more embodiments of the present disclosure. As shown, one or more electronic circuit boards 120 of HMD 100 may include one or more of a power source 121, a processing engine 122, a memory 123, a communications interface 124, and audio source 126, a light source 128, and sensor circuitry 127 operatively coupled with thermistor 114 over cable 116, and one or more other components 125. Though depicted with sensor circuitry 127 operatively coupled to a thermistor 114 over cable 116, HMDs 100 of the present disclosure may include any one or more sensors (whether disposed entirely or partially inside of or exterior to the internal cavity of HMD 100's housing) for measuring physical parameters associated with the animal or the environment within which the animal is located. Such sensors may include, but are not limited to, one or more of a temperature sensors (e.g., thermistors), light sensors (e.g., photodetectors for use with, by way of example, oximeters, retinal scanners, etc.), altitude sensors, pressure sensors, moisture sensors, humidity sensors, motion sensors (e.g., accelerometers), applied force sensors (e.g., strain gauges, etc.), location sensor (e.g., GPS sensor), or any combination of the foregoing for obtaining the measurements desired by the operator for a particular application.

Power source 121 may include any one or more power sources, including any known in the art or hereafter developed. For example, such power sources may include, but are not limited to, a rechargeable battery, a non-rechargeable battery, a removable battery, a solar cell, motion power conversion circuit, etc. Processing engine 122 may include any one or more processing engines, including any known in the art or hereafter developed. For example, such processing engines may include, but are not limited to: processors, microprocessors, microcontrollers, etc. Memory 123 may include any one or more volatile or nonvolatile storage units, including but not limited to: ROM, RAM, flash storage, etc. Communications interface 124 may include any one or more wired or wireless communications transmitters, receivers, transceivers, circuits or communications modules, including any known in the art or hereafter developed. Such communications interfaces 124 may include, but are not limited to: Zigbee communications modules, Bluetooth communications modules, Wi-Fi communications modules, cellular communications modules, etc. Audio source 126 may include any one or more audio sources, including any known in the art or hereafter developed. Such audio sources may include, but are not limited to: a speaker. Light source 128 may include any one or more light sources, including any known in the art or hereafter developed. Such light sources may include, but are not limited to: LEDs, lasers, incandescent light sources, etc. Other components 125 may include any other electronic component desired to be integrated with the HMD 100 to implement system 1000. For example, other components 125 may include additional or alternative sensors, antennae, or other circuitry. In some embodiments, other components 125 may include an electronic ID such as an Electronic Serial Number (ESN), and ID tag, and ID chip, or other componentry to provide a unique identifier for the HMD 100. Such an electronic ID may be associated with a particular animal (for example, based on the animal's ear tag number) to provide receivers 200, computing platforms 300, or client computing devices 500, with added source information to aid in sorting, organizing, storing, and/or otherwise processing information transmitted from a given HMD 100 in an effective manner.

Each of the elements depicted in FIG. 5 may be operatively coupled together to effectuate one or more of the features provided by the present disclosure. For example, thermistor 114 may be operatively coupled with processing engine 122, memory 123, and communications interface 124, for example. Memory 123 may be configured with machine readable instructions which are executed periodically (e.g., on a loop every 15 minutes, for example), and when executed cause processing engine 122 to read/measure a signal transduced or otherwise provided via thermistor 114 (and the related thermistor circuitry, e.g., wires 116, sensor circuitry 127, etc.). The processing engine 122 may, based on machine readable instructions stored in memory 123, cause a discretized data packet to be created from analog electrical signal observed from sensor circuitry 127, and cause the discretized data packet to be transmitted via communications interface 124 (and optionally stored in memory 123) in accordance with an appropriate communications interface protocol (e.g., Zigbee, Bluetooth, Wi-Fi etc.).

FIG. 6 illustrates an example HMD attached to an animal, in this depiction attached to an ear of a cow 700 in accordance with one or more embodiments of the present disclosure. As shown, in some embodiments an HMD 100 may be attached to an animal's ear by piercing the studs 108 of HMD 100 through the scapha or antihelix region of the animal's ear, for example. Cord 114 may be fed into the animal's ear such that thermistor 116 extends into the animal's ear canal to obtain the desired temperature readings. As shown, ear tag identifier 140 associated with the animal 700 may be deployed with the HMD 100 of the present disclosure. The ear tag identifier 140 may be associated with not only the animal of interest, but also associated with an electronic ID of the HMD 100 installed on the animal. In some embodiments, an HMD 100 assigned to one animal may later be reassigned to another animal. For instance, if an animal dies but the operator wants to reuse the deceased animal's HMD 100 to monitor the health of another animal, the operator may reassign the HMD to the new animal (e.g., within system 1000, associate the electronic ID of the HMD with the ear tag identifier 140 of the new animal). As noted previously, associating the right animal with the right HMD 100 may be important for the applications of the technology disclosed herein, depending on the application and needs of the operator. This will become even more clear as other applications and functionality are discussed herein.

Figure 7A:
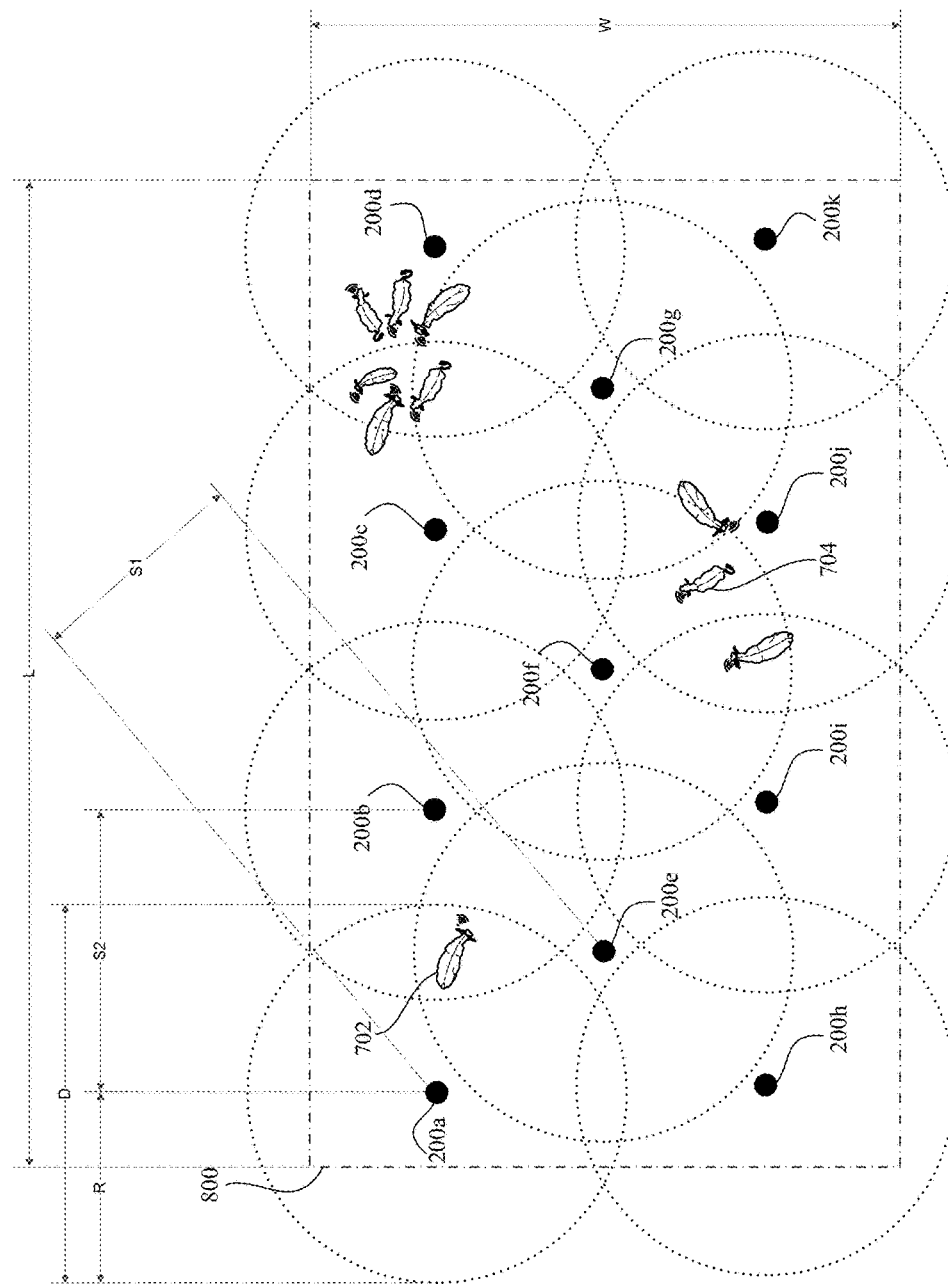
FIG. 7A illustrates an environment within which one or more embodiments of the systems, methods, and apparatus of the present disclosure may be implemented.
Figure 7B:
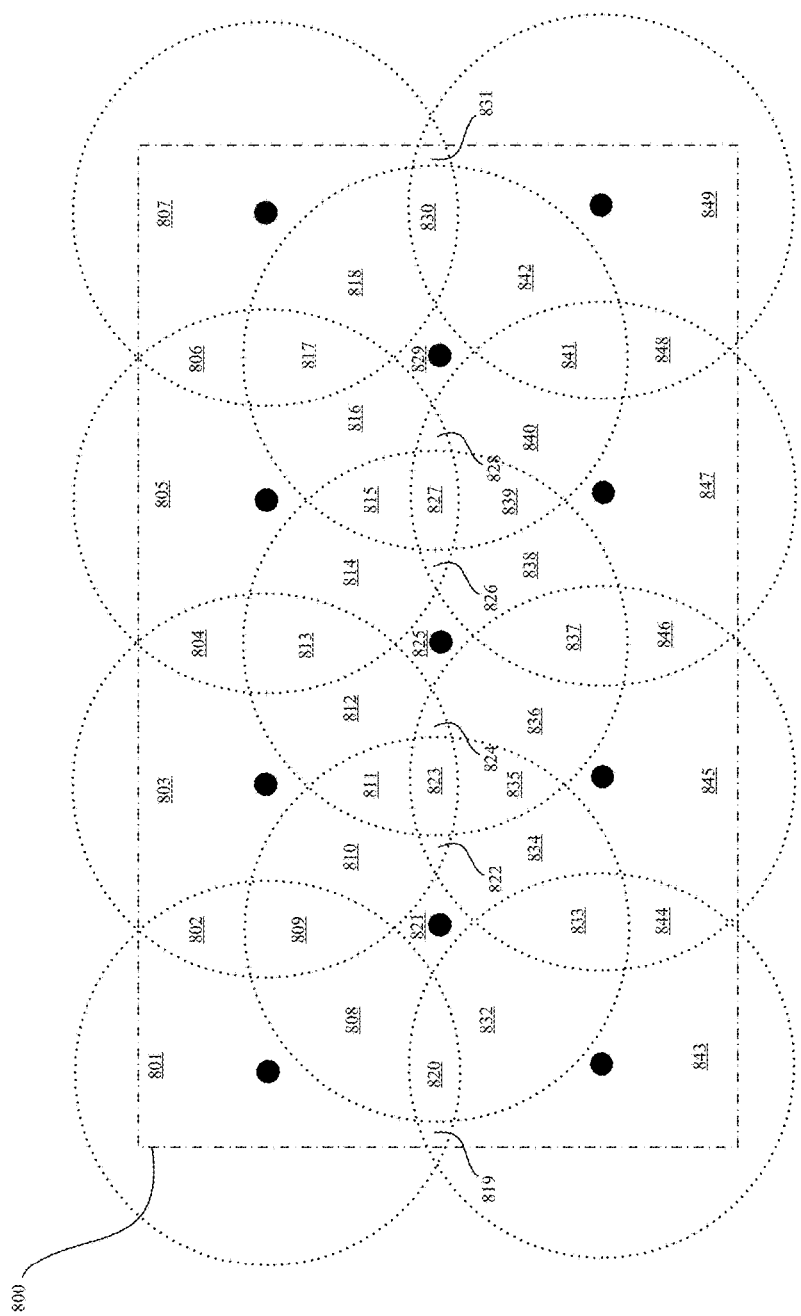
FIG. 7B illustrates the environment depicted in 7A, here demarking example zones for effective signal transmission to or from one or more of the receivers that may be deployed in one or more embodiments of the present disclosure.
Figure 7C:
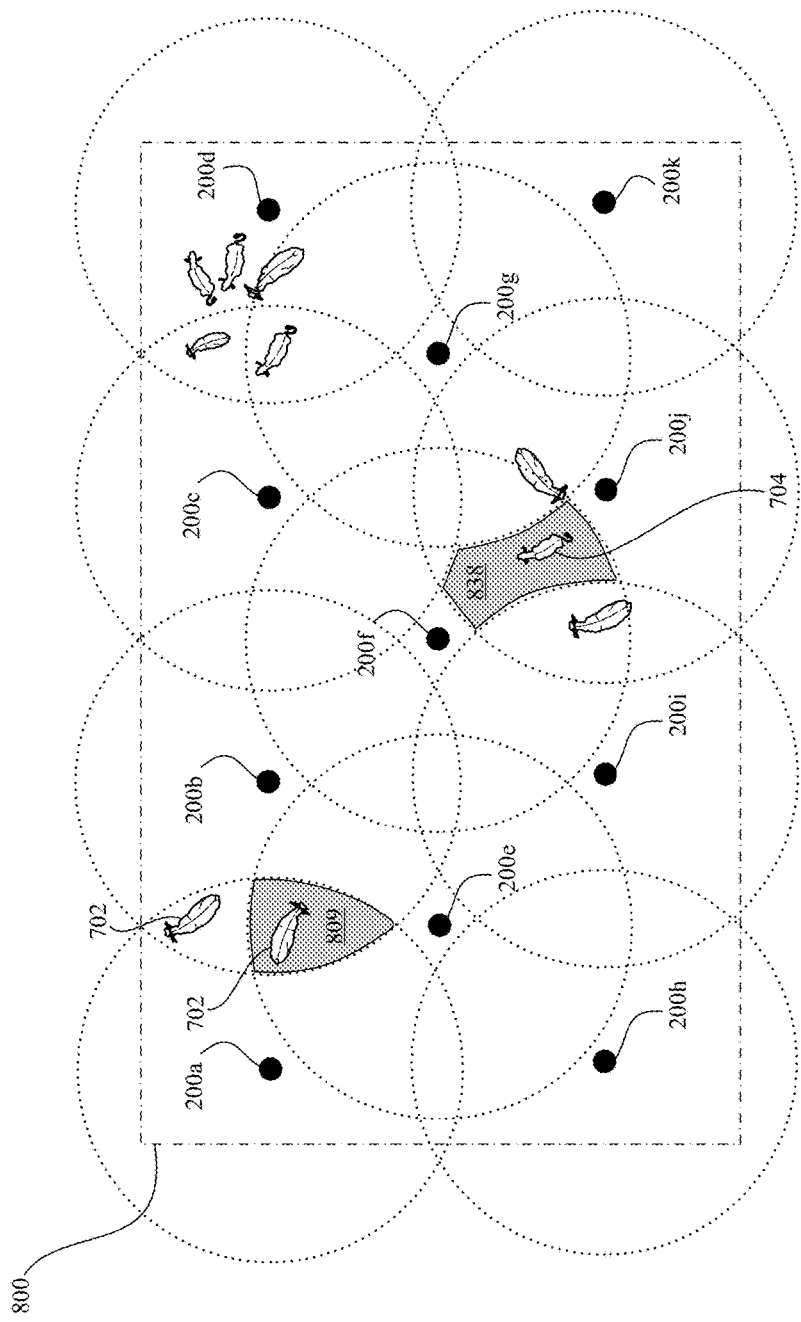
FIG. 7C illustrates the environment depicted in 7B, here depicting one or more animals within the monitored area, and demarking the zones within which some of those animals are located, in accordance with one or more embodiments of the present disclosure.

FIGS. 7A-7C illustrate an example environment within which one or more embodiments of the systems, methods, and apparatus of the present disclosure may be implemented. As these figures depict essentially the same example environment, they will be discussed together with like numerals referring to like elements.

As shown in FIG. 7A, the example environment includes a field 800 containing ten cattle, each with an HMD 100 installed in their ears, each HMD 100 having a thermistor disposed within the ear canal of the respective cow to which it is installed. Installed at various locations throughout the field are a plurality of receivers 200, namely: receiver 200a, receiver 200b, receiver 200c, receiver 200d, receiver 200e, receiver 200f, receiver 200g, receiver 200h, receiver 200i, receiver 200j, and receiver 200k. In the depicted example, the dashed-line circles around each receiver are a symbolic representation of the maximum distance away from each receiver, within which signal transmissions will be successful.

As shown, R may represent the maximum distance within which successful signal communications with an HMD 100 may occur. That is, when an HMD 100 is more than a distance R from a given receiver, the signal transmitted by the HMD 100 will not (or is highly unlikely to) reach the receiver. In configurations where the receivers are configured to poll the HMDs for updates (e.g., the receivers 200 actively transmitting or broadcasting an information request via a transmitter), HMD 100's located beyond a distance R from the polling receiver will not (or are highly unlikely to) receive the transmission. One of ordinary skill in the art will appreciate that the distance R may be limited or defined by the power of the signals that can be generated by the transmitter of the communications interface 124 at the HMDs 100, the power of the signals that can be generated by the transmitter of the communications interface of the relevant receiver 200, or both.

As shown, D may represent the diameter of the circle drawn around each receiver, based on the distance R, delineating the zone within which successful communications between the given receiver and a given HMD 100 may take place. As shown, S1 may represent the distance between a receiver and its nearest neighbor in the receiver network (as depicted in FIG. 7A, S1 is the distance between receiver 200a and receiver 200e), and S2 may represent the distance between a given receiver and its second nearest neighbor (as depicted in FIG. 7A, S2 is the distance between receiver 200a and receiver 200b). In the depicted environment in FIG. 7A, S1<S2 by a small margin. This illustrates that that the distribution of receivers in a given environment need not be perfectly uniform for system 1000 to work properly. While in some embodiments the receiver network may include a substantially uniform distribution of receivers (S1=S2), in other embodiments the receiver network may include a non-uniform distribution of receivers (S1≠S2).

The arrangement of receivers deployed with system 1000 may take any form, e.g., a grid pattern, a hatch pattern, etc. In some embodiments it may be desirable to arrange the position of the receivers 200 within the network such that the zones of successful transmission overlap enough that all the geographic area where the animals are roaming will fall within the successful transmission distance of at least one receiver 200. Some embodiments may call for less coverage, and others more robust coverage, depending on the requirements of the operation. It is well known that electromagnetic signals become attenuated with increased distance of the transmission, and the medium through which the signal must travel. In many applications, such as the one shown in FIGS. 7A-7C, the medium (or the channel through which the transmitted signal travels) is outdoor air. Thus, receiver arrangements configured for increased overlap regions will generally yield an increasingly robust communications environment (i.e., signal transmissions will occur with increasing success). The receiver 200 arrangement may be adjusted according to the needs of the operation, in accordance with one or more embodiments of the present disclosure. Indeed, the present technology may be deployed in any one or more embodiments or implementations that meet the requirements and objectives of the relevant animal caregivers (e.g., operators).

Overlapping zones of successful coverage can result in situations where an HMD 100 is within range of multiple receivers when it transmits a signal. In some embodiments, multiple receivers may receive the signal transmitted by the communications interface 124 of an HMD 100. As described in more detail with reference to the events component 370 of computing platforms 300, system 1000 may utilize such an arrangement to provide enhanced location features to operators. In some embodiments, system 1000 may be able to triangulate or otherwise derive, with varying degrees of accuracy depending on the arrangement of receivers 200, the location of the animal associated with an HMD 100 whose signal transmission was detected by multiple receivers 200.

For example, referring now to FIG. 7B, suppose each segment of field 800 were divided into a plurality of subzones defined by the boundaries of neighboring receivers and the boundary of the field 800. As shown in FIG. 7B, each zone is represented by a numeral in the 800 range. For example, the outer boundaries of subzone 801 are given by the upper left corner boundary lines of the field 800, as well as the dotted lines of the overlapping success zone lines of receiver 200b, receiver 200e, and receiver 200h (i.e., the dotted lines surrounding the solid black bolded line surrounding the subzone numeral, 801. Subzones 802 through 849 are also shown, for reference.

Turning now to FIG. 7C, suppose that a herd of cattle are roaming in field 800. Suppose further that a scheduled signal transmission occurs at 12:00 pm wherein each cow's attached HMD 100 transmits a data packet including the temperature information obtained via each HMD 100's respective thermistor. Each cow's temperatures are received by one or more receivers (depending on overlap), and provided to computing platforms 300, or other elements of system 1000. System 1000 may determine that the temperature readings associated with cow 702 and 704 indicate the onset of a treatable health condition, and may further determine that a given antibiotic should be delivered to cows 702 and 704 within the next five hours, and the system may notify the animal's handler accordingly, discussed in more detail below.

Automatically, or upon request by the animal's handler (via mobile application, text message, internet, or otherwise), the animal's handler may want to know where the relevant animals are located within the field 800. System 1000 may determine that the 12:00 pm transmission by cow 702's HMD 100 was picked up by receiver 200a, receiver 200b and receiver 200e. Based on this information, as well as the zone and subzone region information, system 1000 may determine that cow 702 must be in subzone 809, the only region where all three receivers could have successfully received a transmission from cow 702's HMD 100. Similarly, system 1000 may determine that the 12:00 pm transmission by cow 704's HMD 100 was picked up by receiver 200j and receiver 200f. Based on this information, as well as the zone and subzone region information, system 1000 may determine that cow 704 must be in subzone 838, the only region where both of receiver 200f and receiver 200j could have successfully received the transmission from cow 704's HMD 100 without also being picked up by another receiver.

Accordingly, in some embodiments system 1000 may determine an approximate location for an animal of interest based on which receivers picked up (e.g., received) the relevant HMD 100's signal transmission (or vise versa for the polling configuration). In other embodiments, HMD 100 may include a GPS module. Thus, there are various ways that system 1000 may identify location information about a given animal. Such information may be utilized by system 1000 to provide directions to the handler to find the relevant animal. System 1000 may provide directions as an audible or visual description, and audible or visual instruction, or a visual diagram (e.g., via a route mapping application, or the like). The directions may include step-by-step instructions or a visual route displayed on the handler's client computing device 400 (e.g., the handler's iPhone or other smartphone), and may be based on the handler's current location as provided via a GPS module in the handler's smartphone (which the system 1000 may be configured to access).

As noted previously, HMDs 100 and receivers 200 may be communicatively coupled. That is, they may be equipped with the hardware and software necessary to communicate with one another via their respective communications interfaces in accordance one or more communications protocols known to each. HMDs 100 or receivers 200 or both may further be communicatively coupled, directly or indirectly, with one or more of computing platforms 300 or client computing devices 400. That is, they may be equipped with the hardware and software necessary to communicate with one another via their respective communications interfaces in accordance one or more communications protocols known to each.

Figure 8:
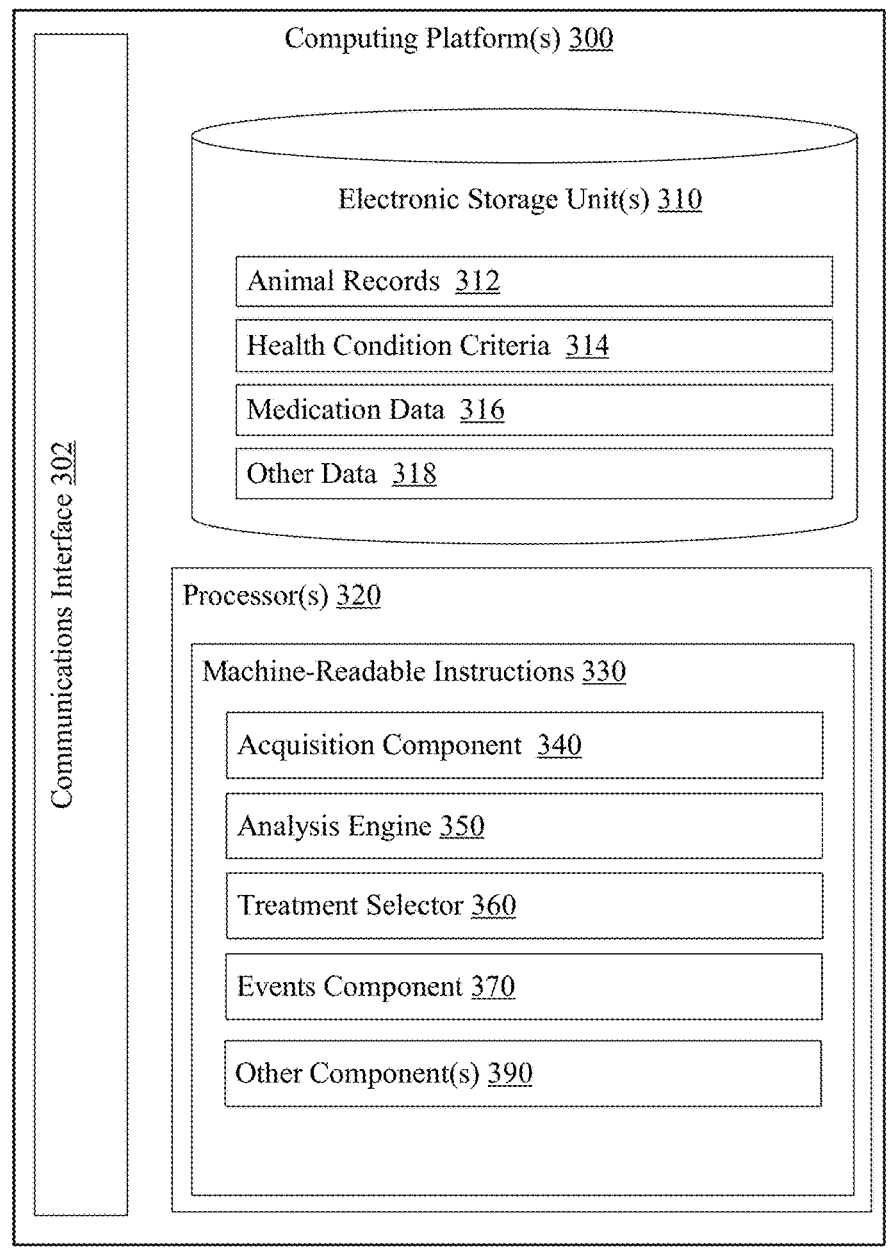
FIG. 8 illustrates an example computing platform that may be implemented in accordance with one or more embodiments of the present disclosure.

FIG. 8 illustrates an example computing platform 300 that may be implemented in accordance with one or more embodiments of the present disclosure. As shown, computing platform(s) 300 may include one or more electronic storage unit(s) 310, one or more physical processor(s) 320, and one or more machine-readable instruction(s) 500. In some embodiments, electronic storage units 310 may store data including, for example as shown in FIG. 1, animal records 312 health condition criteria 314 cost details 316, among other data 318. As shown in FIG. 1, physical processor(s) 320 may be configured by machine-readable instructions 330 to include one or more components that, when executed by physical processor(s) 304, cause or enable computing platform(s) 300 to effectuate one or more of the features described herein.

Such components may include one or more of an acquisition component 340, and analysis component 350, a treatment component 360, an alert component 370, a status component 340, among other components 390. As described herein, any of the components or subcomponents described herein may be in operative communication with one another, as well as with any other element or sub element of the system 1000 (e.g., electronic storage 300, remote computing devices 400, external resources 600, etc.), to effectuate one or more embodiments of the technology disclosed herein.

As shown, electronic storage unit(s) 310 may include animal records 312, among other data and records. Animal records 312 may include static or dynamic information about a specific animal, about a subset of animals within a herd, about a herd generally, or about multiple herds. Such information may include: genetic information (e.g., genus, species, family, subfamily, lineage; breed; ancestry; genetic mutations (albinism, etc.); sex), medical information (e.g., birth date/place, vaccination records, illness records, injury records, allergies, susceptibilities, failed or successful impregnation records, failed or successful birthing records, current and past diseases, current and past operations, current and past treatment regimens, current and past treatment modalities, etc.), phenotype information (pigmentation of fur, hair, skin, eyes, etc.; height; weight; girth; deformities (blindness, dwarfism, protoporphyria, heart condition, respiratory condition, etc.)), geographic information (e.g., birthplace; and each place kept (city, state, zip, farm, ranch, plot, etc.), including length of stay in each place; etc.); temperature information (e.g., an animal's detected body temperature obtained at one or more times in the past, external environmental temperature at one or more times in the past where animal was located); altitude information (altitude or pressure measurements obtained at one or more times in the past where animal was located); feed/diet information (e.g., feed frequency, feed type, feed allotment, feed times, food allergies, etc.), activity information (e.g., daily exercise regimen (for a racehorse, for example)), production information (e.g., amount of milk a milk cow produced in a given time period, etc.), or any other information, or any other information that can be associated with the animal including financial information (e.g. price paid for animal, costs incurred in connection with animal, revenue/profits generated from animal, etc.), responsible employee information (e.g., responsible ranch hand's name, number, email address (or other contact or personal information), shift hours, scheduled time off, sick day (or other work related information)), or customized predefined metrics (e.g., lung score, heart score, speed score, sleep score, production score).

It should be noted that animal record 312 may include manually entered information (e.g., an end user entering information into a data field via a remote computing device 400 and uploading it to computing platform(s) 300), automatically obtained information (e.g., biometric information detected via sensor apparatus 100 about a particular animal may be automatically communicated to computing platform 300 and updated in the corresponding animal record 312 stored in electronic storage unit(s) 310), automatically generated information (e.g., information based on or derived from any entered or otherwise obtained information), or in any combination of the foregoing or other desirable manner (e.g., an end user may select, via their remote computing device 400, an option to sync the computing platform 300 with an external resource 600 such that the computing platform 300 is updated with information from, for example, an online database accessible through an Internet connection).

For example, an animal record for a cow on a farm may include an entry in the animal record for the cow's date of birth, and the cow's current age. The date of birth may be manually entered to a newly created animal record shortly after the given cow is born. The cow's age may be automatically updated as computing platform 300 automatically obtains current date information (e.g., from an external resource such as an online calendar) and automatically generates an entry for the cow's age based on the difference in the current date and the cow's date of birth. One of skill in the art will appreciate that the animal record 312 may include both static information, or in other words unchanging information (e.g., animal date of birth), and active or dynamic information, information that is subject to change based on other occurrences (e.g., animal age based on the passage of time). Additionally, one of skill in the art will appreciate that the information maintained in animal records 312 may configured such that it is as condensed or extensive as desired by the end user (e.g., as desired by the client, the owner, the farmer, the ranch operation, etc.).

The information maintained in animal records 312 may be entered manually (e.g., an end user entering information into a data field via a remote computing device 400 and uploading it to computing platform(s) 300), updated automatically (e.g., biometric information detected via sensor apparatus 100 about a particular animal may be automatically communicated to computing platform 300 and updated in the corresponding animal record 312 stored in electronic storage unit(s) 310), or in any other desirable manner (e.g., an end user may select, via their remote computing device 400, an option to sync the computing platform 300 with an external resource 600 such that the computing platform 300 is updated with information from, e.g., an online database accessible through an Internet connection.

As further shown in FIG. 8, electronic storage unit(s) 310 may include health condition criteria 314, among other data and records. Health condition criteria 314 may include relationships between animal categories, animal parameters, and health conditions.

Animal categories may be defined with as much or as broadly or narrowly as desired for a given application. For example, an animal category may be defined by a genus, e.g. Bos, or a subfamily within a genus, e.g., Bovinae, or a member group within a subfamily, e.g. Cattle. In some embodiments, the animal category may be much more specific than simply the genus, species, or subfamily, for instance by drilling down into more specific details as to any of the types of information described above with regard to animal records. For example, an animal category may be defined as: male cattle with black and white spotted hides between the ages of 6 and 9 and weighing between 2000 and 2500 pounds. A person of ordinary skill in the art will appreciate upon reading this disclosure that animal categories can be defined with as much granularity as desired for a given application, including with specificity as to any of the various types of information discussed herein with respect to animal records, among other information. The present disclosure is intended to extend to all such animal categories, defined in any manner desired for a given application.

Animal parameters include any attribute about an animal, or about an animal's environment, that may be quantifiably measured. For instance, an animal parameter may include the animal's core temperature, heart rate, perspiration, activity (e.g., speed), geographic location (e.g., GPS coordinates, altitude, etc.), ambient temperature, wind-chill, etc.

Health conditions include any condition that describes the state of a structure or function of a living organism's body. Health conditions can include any type of disease, illness, symptom, injury, mutation, or otherwise, whether ongoing, chronic, temporary or permanent. To illustrate exemplary how health condition criteria may, in some embodiments, be define relationships between animal categories, animal parameters, and health conditions, consider the following form of an exemplary health condition criteria: for [animal category], a [animal parameter] exceeding [range] for [time], is associated with [health condition]. For example: for cattle having entirely black hides, a core body temperature exceeding 102.5 degrees Fahrenheit for more than 3 hours but less than 5 hours is associated with Bovine Respiratory Disease Complex (BRDC). Of course, as one of ordinary skill in the art will appreciate, the health condition criteria may be defined with as much granularity as desired or as understood for a particular animal category. The health condition criteria may be readily defined in software and/or stored in hardware.

As described in more detail below, health condition criteria, if satisfied, may indicate the animal associated with the measured attribute is developing (or has already developed) the associated health condition and may need some form of treatment.

As further shown in FIG. 8, electronic storage unit(s) 310 may include medication data 316, among other data and records. Medication data 316 may include static or dynamic information about medications that may be applied or provided to an animal with a given health condition. Such static or dynamic information can be pricing information about a given medication (e.g., price paid for lots of the medication, current market price to purchase more, etc.), availability information (e.g., amount of the given medication currently in stock, amount of the given medication available from a particular seller or group of sellers, contact or website information through which more of a given medication may be purchased, delivery times or estimated delivery dates for orders of a given drug, etc.), effectiveness (e.g., effectiveness for treating a given health condition generally, for a given health condition for an animal of a particular animal category, for a given health condition for an animal of a particular animal category with a given measure of animal parameters), etc. Medication data may be entered manually (e.g., farm hand manually inputting updates about the stock of medication maintained at the farm after the farm hand has used up some of the stock of the drug by treating an animal with a health condition) or may be updated automatically (e.g., receiving updates to dynamic information, such as current market pricing, updated research findings/warnings about a given drug, or newly discovered symptoms or side effects for certain drugs, updated instructions for delivery of a given medication that may be obtained from an external resource 600 such as an online database).

As further shown in FIG. 8, computing platform(s) 300 may include one or more physical processor(s) 320 configured with machine-readable instruction(s) 500 which, when executed, effectuate one or more of the features of the present disclosure. In some embodiments, machine-readable instruction(s) 500 may include an acquisition component 340, an analysis engine 350, treatment selector 360, events component 370, hardware status component ("HW status component") 380, among other components 390.

Acquisition component 332 obtains data representing physical measurements detected and transduced by sensor apparatus 100. Acquisition component 332 may obtain acquisition component 332 may be operatively coupled with a communications interface (discussed in detail in the disclosure that follows) that receives signals, either directly or indirectly, from sensor apparatus 100. Acquisition component 332 may obtains it's such data periodically on an automated basis, or any given time upon a user-initiated request. Acquisition component 332 may associate the measurement, permanently or temporarily, with the animal record 312 stored in electronic storage 330. Optionally, acquisition component 332 may determine whether the physical measurement was accurately obtained.

In one example, acquisition component 332 may determine whether the physical measurements fall within a realistic range. For instance, a range of realistic body temperatures for a given type of cattle may be stored in electronic storage 332 as being between 70 and 100 degrees Fahrenheit, and when acquisition component 332 obtains data representing a given cow's body temperature of 200 degrees Fahrenheit, Acquisition component 332 may determine that the measured temperature is outside the realistic range, and filter out or otherwise discard the data as null.

In another example, the acquisition component 332 may determine whether the sensor apparatus 100 is operating properly (based on status component 380, for example, as discussed below). If acquisition component 332 determines that the physical measurement was obtained during a time when the sensor apparatus was not working properly, or was otherwise malfunctioning, the acquisition component may filter out or otherwise discard the data as null.

Analysis engine 334 determines whether one or more health condition criteria 314 have been satisfied for a given animal being monitored by sensor apparatus 100. Extending the example above—where the health condition criteria was described as: for cattle having entirely black hides, a core body temperature exceeding 102.5 degrees Fahrenheit for more than 1 hour is associated with Bovine Respiratory Disease Complex (BRDC)—suppose that one of a farmers entirely black hided cattle has an ear tag numbered 702 which has been associated with a sensor apparatus 100 installed on the cow's ear. Suppose also that the sensor apparatus 100 measures cow 702's core temperature and transmits a signal representative of that temperature on a periodic basis, e.g., every 15 minutes, for reception by a receiver. Either through direct or indirect reception, acquisition component 340 obtains the temperature information that is obtained, e.g., every 15 minutes, and may optionally facilitate storage of the information in the animal record associated with cow 702 in one or more electronic storage unit(s) 310. Analysis engine 334 may monitor the temperature readings obtained by acquisition component 340, evaluate those temperature readings with respect to the health condition criteria 314, and determine whether one or more health condition criteria 314 have been satisfied. Again, referring to the example above, suppose that the following measurements have been obtained from sensor apparatus 100 installed on cow 702's ear over the course of a four-hour period:

| ANIMAL RECORD_LIVESTOCK ID 702_TEMPERATURE DATA | | | | | |
|---|---|---|---|---|---|
| A | B | C | D | E | F |
| 1 Date | Time | Core Temp. | Ambient | | |
| 2 Aug. 26, 2017 | 12:00 | 101.5° F. | 78° F. | ... | ... |
| 3 Aug. 26, 2017 | 12:15 | 101.5° F. | 78° F. | | |
| 4 Aug. 26, 2017 | 12:30 | 102° F. | 78° F. | | |
| 5 Aug. 26, 2017 | 12:45 | 102.5° F. | 78° F. | | |
| 6 Aug. 26, 2017 | 1:00 PM | 102.5° F. | 79° F. | | |
| 7 Aug. 26, 2017 | 1:15 PM | 102.7° F. | 79° F. | | |
| 8 Aug. 26, 2017 | 1:30 PM | 102.7° F. | 79° F. | | |
| 9 Aug. 26, 2017 | 1:45 PM | 102.7° F. | 78° F. | | |
| 10 Aug. 26, 2017 | 2:00 PM | 102.9° F. | 78° F. | | |
| 11 Aug. 26, 2017 | 2:15 PM | 102.9° F. | 78° F. | | |
| 12 Aug. 26, 2017 | 2:30 PM | 103° F. | 78° F. | | |
| 13 Aug. 26, 2017 | 2:45 PM | 102.8° F. | 77° F. | | |
| 14 Aug. 26, 2017 | 3:00 PM | 102.8° F. | 77° F. | | |
| 15 Aug. 26, 2017 | 3:15 PM | 102.7° F. | 77° F. | | |
| 16 Aug. 26, 2017 | 3:30 PM | 102.8° F. | 77° F. | | |
| 17 Aug. 26, 2017 | 3:45 PM | 102.9° F. | 77° F. | | |
| 18 Aug. 26, 2017 | 4:00 PM | 102.7° F. | 77 F. | | |

As may be seen from the table of temperature data for cow 702 above, the core temperature reading from the sensor apparatus 100 first begins to exceed the temperature threshold of 102.5° F. defined in the health condition criteria at approximately 1:15 pm on Aug. 26, 2017 and continues to increase without ever falling back to 102.5 or below ° F. Based on the predefined health condition criteria 314, analysis engine 350 may determine that health condition criteria has been satisfied for the BRDC disease. In other words, analysis engine processes the information obtained from sensor apparatus 100 (via acquisition component 340, or otherwise), and generates a diagnosis, if any, of a health condition that the respective animal may be developing (or have already developed) based on the predefined health condition criteria 314.

It should be appreciated by those of skill in the art that the scenario described above with respect to cow 702 is a simple example that is in no way intended to be limiting of the scope of the present disclosure. Instead, a person of skill in the art will appreciate upon reading this disclosure, just as the health condition criteria 314 can be as granular or detailed as desired, so to can the analysis engines 350 evaluation that informs the ultimate diagnosis, or potential diagnosis based on any and all of the information available to system 1000.

Once analysis engine 350 has determined that one or more health condition criteria 314 have been satisfied for a given animal, treatment selector 360 determines which treatment modality to apply to the given animal under the circumstances. There may be many treatment options will available for the identified health condition, and treatment selector 360 may consider various factors and draw on various pieces of information in identifying an appropriate treatment modality under the circumstances. The various pieces of information that treatment selector 360 may consider includes any and all of the information accessible to system 1000. In some embodiments treatment selector 360 may determine which of two or more treatment modalities should be applied based on one or more factors.

In some embodiments treatment selector 360 may rank competing treatment modalities based on one or more factors. In some embodiments the factors that treatment selector 360 may consider may be defined, in whole or in part, by default. In some embodiments the factors that treatment selector 360 may consider our defined, in whole or in part, by an end user (e.g., a farmer who has adopted system 1004 monitoring is livestock). The following three examples to help illustrate just a few of the factors treatment selector 360 may assess in its evaluation as to what treatment modality is to be selected.

For example, suppose that analysis engine has determined that cow 702 has developed a health condition, Bacterial Infection X. Treatment Selector 360 may draw on medication data 316 to determine which medications are designated for use to treat Bacterial Infection X. Treatment Selector 360 may identify six different antibiotics that are appropriate for treating Bacterial Infection X. Treatment Selector may pull information from the animal record for cow 702 to identify any factors that weigh for or against any one of the six different antibiotics. For example, animal record for cow 702 may include a medical report indicating that cow 702 has a fatal allergy to an active ingredient in antibiotic 1 and antibiotic 3, and a non-fatal allergy to an active ingredient in antibiotic 2, leaving antibiotics 4, 5, and 6 as the only options that are not known to cause an allergic reaction in cow 702. Treatment Selector 360 may pull information from the medication data 316 to determine how quickly the animal should be treated for best results.

For example, treatment selector 360 may pull information from medication data 316 that indicates, Bacterial Infection X is highly contagious 24 hour after onset absent an antibiotic. Treatment selector 360 may obtain the size of the herd cow 702 is a member of based on the Animal Records data, and determine that one of antibiotics 4, 5, and 6 should be given to the animal within the next two hours. Treatment selector 360 may draw again on the medication data 316 to determine which of the antibiotics are currently in stock (such that they could reasonably be given to the animal within the two-hour timeframe). Treatment selector 360 may determine that antibiotics 3, 4 and 6 are currently in stock at the farm, antibiotic 1 is out of stock at the farm but can be brought to the farm by a courier at a local vendor within 5 hours, antibiotic 2 is out of stock and not shippable or deliverable, and antibiotic 5 is out of stock and can be shipped with a guaranteed delivery time of 48 hours.

Treatment selector may further draw on medication data 316 to determine pricing information for the antibiotics. Treatment selector may determine that the cost for the twice a day for five day delivery regimen for antibiotic 1 is $5.00, the cost for the once a day for seven day delivery regimen for antibiotic 2 is $20.00, the cost for the three times a day for two day delivery regimen for antibiotic 3 is $60.00, the cost for the once a day for seven day delivery regimen for antibiotic 4 is $60.00, the cost for the three times a day for two day delivery regimen for antibiotic 5 is $55.00, the cost for a one-time only dose of antibiotic 6 is $65.00. Treatment selector may eliminate antibiotics 1, 2 and 3 on account of cow 702's allergies; may eliminate antibiotic 5 because it is not in stock at the farmhouse and thus cannot meet the imminent delivery timetable to prevent the infection from spreading to other cattle in the herd; and treatment selector may eliminate antibiotic 6 because it is the most expensive, and thus may select antibiotic 4 as the treatment for cow 702. Thus, treatment selector may determine which treatment modality to apply to the cow based on a process of elimination approach based on various considerations.

Alternatively or additionally, treatment selector 360 may rank the competing treatment modalities. This may be done in any desired manner, applying any desired priority based on the application and the end user's interests. For example, the rank may be based on a weighted score that accounts for various factors of interest. For instance, consider the following scoring that takes the scores for N factors of interest, weights the scores according to a weighting factor, $w_N$, then sums them up to obtain the overall score for the given treatment modality, MODALITY SCORE.

$$\text{MODALITY SCORE} = (\text{Factor1}_{score})w_1 + (\text{Factor2}_{score})w_2 + \ldots + (\text{FactorN}_{score})w_N \quad [1]$$

For the given factors of interest, e.g., allergies, availability, cost, the initial score, FactorN$_{score}$, may be given by any formula, which may or may not include further weighting in addition to the weighting factor, $w_N$, applied later in equation 1. For example, if allergies were Factor 1, availability of the medication were Factor 2, and cost were Factor 3, an example treatment selector may apply the following:

$$\text{Factor1}_{score} = \text{allergies}_{score} = \begin{cases} 0.0, & \text{fatal allergy} \\ 0.5, & \text{nonfatal allergy} \\ 1.0, & \text{no allergy} \end{cases} \quad [2]$$

$$\text{Factor2}_{score} = \text{availability}_{score} = \begin{cases} 0.0, & \text{Out of Stock; Not Deliverable} \\ 1/x, & \text{Out of Stock; Deliverable within } [x] \text{ hours} \\ 1.0, & \text{In Stock} \end{cases} \quad [3]$$

$$\text{Factor3}_{score} = \text{cost}_{score} = \frac{1}{[x]} * 1.075, \quad [4]$$

$[x]$ = price for medication regimen

Extending the examples above, suppose treatment selector accesses various information from system 1000 and applies the example algorithms above with respect to each of the six antibiotics with respect to cow 1902. Suppose also, for simplicity, that weighting factors $w_1$, $w_2$, $w_3 = 1$.

|  | allergies$_{score}$ | availability$_{score}$ | cost$_{score}$ | Modality SCORE |
|---|---|---|---|---|
| Antibiotic 1 | 0 = 0 | 1/[5] = 0.2 | (1/[$5]) * 1.075 = 0.2150 | 0.4150 |
| Antibiotic 2 | 0.5 | 0 | (1/[$20]) * 1.075 = 0.0538 | 0.5538 |
| Antibiotic 3 | 0 | 1 | (1/[$60]) * 1.075 = 0.0179 | 1.0179 |
| Antibiotic 4 | 1 | 1 | (1/[$60]) * 1.075 = 0.0179 | 2.0179 |
| Antibiotic 5 | 1 | 1/[48] = 0.02 | (1/[$55]) * 1.075 = 0.0195 | 1.0395 |
| Antibiotic 6 | 1 | 1 | (1/[$65]) * 1.075 = 0.0165 | 2.0165 |

Thus, treatment selector 360 may determine a rank of six antibiotics identified as appropriate for treating Bacterial Infection X in cow 702 as:

|  | RANK |
|---|---|
| Antibiotic 4 | 1 |
| Antibiotic 6 | 2 |
| Antibiotic 5 | 3 |
| Antibiotic 3 | 4 |
| Antibiotic 2 | 5 |
| Antibiotic 1 | 6 |

As shown in the example table above, treatment selector 360 has determined that Antibiotic 4 is the treatment modality most appropriate for cow 702 under the circumstances. Although the example ranking approach and the example elimination approach applied by treatment selector 360 shown above both identified Antibiotic 4 as the most desirable alternative among the existing options, this need not always be the case. Indeed, one of ordinary skill in the art will appreciate that the expressions above are merely exemplary, and any modifications, variations, or other algorithms may be applied to account for the considerations of greatest import for a given application.

For instance, a smaller farming operation may be more interested in the cost of a given treatment modality, and thus may use a different expression to compute a score for that factor (or may apply a much higher weight, $w_3$, to that score when computing the MODALITY SCORE in accordance with the formulae above), for example. By way of another example, a farmer who doesn't have a large workforce to go around applying the treatment modality to all the sick animals may opt to include a factor that accounts for the number of doses each antibiotic regimen requires, and assign a higher score to those treatment modalities that require the least number of doses.

In another example, the treatment selector 360 may generate a herd-specific effectiveness score. For example, treatment selector 360 may draw on animal records for the herd within which cow 702 resides, and compute a score that represents how effective the given treatment modality has been within the particular herd. This provides farmers with much more intuitive information for their specific herds. For instance, antibiotic 4 may have previously been given to 7 other cows in the same herd, and in all but one case the cattle died; while antibiotic 6 may have been given to 10 cows in the herd, and in all but one case the cattle returned to full health. Thus, the treatment selector 360 may compute a herd specific effectiveness score for antibiotic 4 of, e.g., 1/7=0.14, and for antibiotic 6 of, e.g., 9/10=0.9. Thus, if a farmer had also included a factor such as herd-specific effectiveness in the computation of the MODALITY SCORE, the ranking procedure would've ranked antibiotic 6 highest, despite it being a more expensive drug than antibiotic 4.

In some embodiments, such data may be collected and shared among farmers in particular regions, or with veterinarians throughout various regions. This way, as between competing treatment modalities, the more effective options may be selected based on relevant prior usage, regardless of what the underlying physiological rationale is behind the choice. Thus, the present technology gives farmers and ranch operators (among others) the flexibility and tools to more carefully and precisely care for their animals, and make more intelligent decisions when treating health conditions. Their decisions can be based on any of the information discussed in the present disclosure.

In some embodiments the treatment selector 360 may provide the results of its determination as an update on a website accessible by the relevant employees or managers involved in farm operation. In some embodiments, the treatment selector 360 provides its determinations to an events component that coordinates tasks items and reporting that aid in ensuring that the relevant animal obtains the relevant treatment. In some embodiments, treatment selector 360 provides its determinations to designated veterinarian(s) who can (i) confirm or deny that the determined treatment modality is appropriate (ii) make a change to the treatment modality determined by the treatment selector 360 (e.g., change the selection to antibiotic 5 based on factors not yet known to system 1000 but known to the veterinarian), (iii) prescribe the medication corresponding to the selected/determined treatment modality (if a prescription is necessary), or (iv) leave comment or notes, etc.; any and all of the foregoing can be transmitted back to the computing platform 300, and can optionally be stored in an animal record sector or elsewhere on electronic storage 310.

As further shown in FIG. 8, computing platform(s) 300 may include an events component 370. Once analysis engine 350 has determined that one or more health condition criteria 314 have been satisfied for a given animal, and once treatment selector 360 determines which treatment modality to apply to the given animal under the circumstances, events component 370 may generate requests, updates, notifications, alerts (and processes input received back responsive to the same) to seamlessly coordinate task items and reporting that aid in ensuring that the relevant animal obtains the relevant treatment, and that relevant updates are made to animal records 312 as relevant events occur.

In some embodiments, events component 370 may obtain the determination made by treatment selector 360 (and optionally confirmed by a designated veterinarian), and, based on information obtained from electronic storage units 310 about the animal's handler(s) (e.g., employees, managers, supervisors, etc.), generate and effectuate transmission of a notification to the animal's handler to put them on notice of the animal's health condition, and provide instruction on next steps for the handler. The notification may be provided to the handler(s) in any one or more manners desired—e.g., SMS, email, automated phone call, broadcast, mobile application, etc.

For example, events component 370 may, obtain a determination from treatment selector 360 that cow 1902 has developed a health condition, and is in need of antibiotic 4 within the next two hours. Events component 370 may access electronic storage 310 and identify that an employee named Clayton is the assigned handler for the animal, and that Clayton's mobile phone number is (123) 456-7890. Events component 370 may automatically generate a text message using a format such as: "Hi [Handler], [animal ID] you are assigned to appears to have developed [health condition] and is in need of the following treatment: [delivery format/site] of [treatment modality] within the next [time-limit] (i.e., before [local time corresponding to time limit]); [treatment modality] can be found at [location/description]; feel free to call your supervisor [Supervisor] at [number] if you have any questions or concerns." Thus, events component 370 may generate and facilitate transmission of a text message to Clayton that says: "Hi Clayton, cow 1902 you are assigned to appears to have developed Bacterial Infection X and is in need of the following treatment: intravenous delivery of Antibiotic 4 in one of the cow's hind quarter within the next 2 hours (i.e., before 4 pm today); Antibiotic 4 can be found at Barn C in the blue syringes on the south wall, labeled Antibiotic 4 in bold lettering; feel free to call your supervisor Jake at (789) 123-4567 if you have any questions or concerns." This is just one example, as will be appreciated by those of skill in the art, and any variations or modifications to include more or less information may be implemented within the scope of the present disclosure.

Events component 370 may operate with enhanced features depending on the platforms accessible to it. For instance, system 1000 may include an animal monitoring mobile application configured to provide a series of enhanced functionality to managers, supervisors, and other handlers to improve the efficiency with which care of relevant animals is carried out. Such a mobile application may provide a host of optional tools to help the handler once a notification has been received.

For instance, if a notification similar to the aforementioned text message is sent to a handler through an animal monitoring mobile application, the application may include options for the handler to (i) obtain delivery information describing or depicting how to deliver the treatment modality to the animal (e.g., written instructions, linked video tutorial, etc.), (ii) obtain location information depicting or describing where the animal is on the property (may include map and route information based on GPS or triangulation via receivers 200, (iii) activate one or more visible light sources or audible audio sources associated with the animal to assist the handler in locating the animal, (iv) obtain warning information about the animal such as the animal's level of aggressiveness, (v) reassign one or more tasks to another backup handler if for one reason or another the first handler cannot complete the required tasks, (vi) request assistance from nearby handlers on the property during a task, (vii) scan the barcode on the relevant treatment modality used (the Antibiotic packaging) when pulled from the stock room so that stock information can be updated, (viii) confirm when any one or more relevant tasks has been completed (e.g., to stop reminders if reminder alerts have been activate), (ix) accept a calendar invitation that places the work item in the users mobile calendar with an associated alert/reminder, (x) provide customized comments or notes about the animal (e.g., "the animal's ear appears to be cut and bleeding, so the temperature readings from the sensor may have been erroneous," "when I showed up to deliver the antibiotic, the animal was dead," or "the cow appears to have a cut on its left leg and walks with a considerable limp that a vet should probably treat"), or (xii) any other desired interactivity.

Referring to FIGS. 1-8 collectively, although these illustrate example embodiments with components, elements and circuits partitioned in the depicted manner, it will be appreciated by one of ordinary skill in the art that various components and circuits of the system 1000, HMD 100, and subsystems described herein may be implemented utilizing any form of hardware, software, or a combination thereof. For example, one or more processors, controllers, ASICs, PLAs, PALs, CPLDs, FPGAs, logical components, software routines or other mechanisms, including associated memory, might be used to implement one or more components or circuits in embodiments of the system 1000 or HMD 100, or other components of the present disclosure. In embodiments, the various components and circuits described herein might be implemented as discrete components or the functions and features described can be shared in part or in total among two or more components. In other words, as would be apparent to one of ordinary skill in the art after reading this description, the various features and functionality described herein may be implemented in any given application and can be implemented in one or more separate or shared components in various combinations and permutations. Even though various features or elements of functionality may be individually described or claimed as separate components, in various embodiments these features and functionality can be shared among one or more common software and hardware elements, and such description shall not require or imply that separate hardware or software components are used to implement such features or functionality.

HMDs or other system elements of the present disclosure might include, for example, one or more processors, controllers, control modules, or other processing devices. Such might be provided by general-purpose or special-purpose processing engines such as, for example, a microprocessor, controller, or other control logic.

HMDs or other system elements of the present disclosure might include one or more memory modules, simply referred to herein as memory. For example, memory might include random access memory (RAM) or other dynamic memory which might be used for storing information and instructions to be executed by a processing engine of a HMD or other system elements. Memory might also be used for storing temporary variables or other intermediate information during execution of instructions to be executed by the HMDs' or other system elements' processing engine. Memory might likewise include a read only memory ("ROM") or other static storage device coupled to a bus for storing static information and instructions for an associated processor.

It will be understood by those skilled in the art that the HMDs or other system elements of the present disclosure might include one or more various forms of information storage mechanism, which might include, for example, a media drive and a storage unit interface. The media drive might include a drive or other mechanism to support fixed or removable storage media. For example, a hard disk drive, a solid-state drive, a magnetic tape drive, an optical disk drive, a CD, DVD, or Blu-ray drive (R or RW), or other removable or fixed media drive might be provided. Accordingly, storage media might include, for example, a hard disk, a solid-state drive, magnetic tape, cartridge, optical disk, a CD, DVD, Blu-ray or other fixed or removable medium that is read by, written to or accessed by media drive. As these examples illustrate, the storage media can include a computer usable storage medium having stored therein computer software or data.

In alternative embodiments, information storage mechanisms that may be implemented in one or more embodiments of the present disclosure might include other similar instrumentalities for allowing computer programs or other instructions or data to be loaded into one or more computing components of HMDs or other system elements. Such instrumentalities might include, for example, a fixed or removable storage unit and an interface. Examples of such storage units and interfaces can include a program cartridge and cartridge interface, a removable memory (for example, a flash memory or other removable memory module) and memory slot, a PCMCIA slot and card, and other fixed or removable storage units and interfaces that allow software and data to be transferred from the storage unit to the HMD or other system elements (e.g., to a memory of the HMD).

As described herein, and as one of ordinary skill in the art will appreciate, HMDs or other system elements of the present disclosure might include a communications interface. Such communications interfaces might be used to allow software and data to be transferred between the HMDs or other system elements and external devices or resources. Additional nonlimiting examples of communications interfaces might include a modem or softmodem, a network interface (such as an Ethernet, network interface card, WiMedia, IEEE 802.XX or other interface), a communications port (such as for example, a USB port, IR port, RF port, RS232 port Bluetooth® interface, or other port), or other communications interfaces. Software and data transferred via a communications interface might typically be carried on signals, which can be electronic, electromagnetic (which includes optical) or other signals capable of being exchanged by a given communications interface. These signals might be provided to the communications interface via a channel. This channel might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium," "machine readable medium" and "computer usable medium" are used to generally refer to transitory or non-transitory media such as, for example, memory, storage unit, media, and channel discussed above. These and other various forms of computer program media, computer readable media, or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable HMDs or other system elements to perform features or functions of the present application as discussed herein.

While various embodiments of the disclosed technology have been described above, it should be understood that they have been presented by way of example only, and not of limitation. Likewise, the various diagrams may depict an example architectural or other configuration for the disclosed technology, which is done to aid in understanding the features and functionality that can be included in the disclosed technology. The disclosed technology is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the technology disclosed herein. Also, a multitude of different constituent module and component names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the terms "module" or "component" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. An intelligent health monitoring engine comprising:
a processor;
a memory;
a power source;
a communications interface to receive data from a remote intelligent health monitoring device;
a non-transitory computer readable medium storing machine readable instructions that, when executed by the processor, cause the intelligent health monitoring engine to:
acquire temperature data associated with an animal based on one or more temperature measures obtained by remote intelligent health monitoring device;
determine whether the temperature data acquired satisfies a health condition criteria;
identify a treatment modality to be delivered to the animal to treat a health condition if a health condition criteria has been satisfied;
identify a caregiver for the animal;
provide treatment modality information to the caregiver;
wherein the processor, the memory, the power source, and the communications interface, are operatively coupled together and held within an internal cavity, at least two or more of which are separately releasable from within the internal cavity.

2. The intelligent health monitoring engine of claim 1, wherein the remote intelligent health monitoring device is attached to an ear of the animal, and the temperature data is based on heat sensed within the ear canal of the animal.

3. The intelligent health monitoring engine of claim 1, wherein the health condition criteria comprises a temperature threshold.

4. The intelligent health monitoring engine of claim 1, wherein determining whether temperature data satisfies a health condition criteria is based upon one or more of an ambient temperature near a location of the animal, and a length of time during which the temperature data satisfied the health condition criteria.

5. The intelligent health monitoring engine of claim 1, wherein identifying a treatment modality to be delivered to the animal to treat a health condition is based on one or more of: a breed of the animal, an age of the animal, a size of the animal, a treatment history of the animal, and a known allergy of the animal.

6. The intelligent health monitoring engine of claim 1, wherein identifying a treatment modality to be delivered to the animal to treat a health condition is based on one or more of: the treatment's availability, effectiveness, and cost.

7. The intelligent health monitoring engine of claim 1, wherein identifying a treatment modality to be delivered to the animal to treat a health condition comprises selecting among a plurality of medications to deliver to the animal.

8. The intelligent health monitoring engine of claim 1, wherein providing treatment modality information to the caregiver comprises: generating one or more of a text message, an email, or a phone call describing the treatment modality information.

9. The intelligent health monitoring engine of claim 1, wherein treatment modality information comprises one or more of: a medication type, availability, dosage, and delivery site.

10. An intelligent health monitoring engine comprising:
a processor;
a memory;
a power source;
a communications interface to receive data from a remote intelligent health monitoring device;
a non-transitory computer readable medium storing machine readable instructions that, when executed by the processor, cause the intelligent health monitoring engine to:
acquire temperature data associated with an animal based on one or more temperature measures obtained by remote intelligent health monitoring device;
determine whether temperature data satisfies a health condition criteria;
identify a treatment modality to be delivered to the animal to treat a health condition if a health condition criteria has been satisfied;
identify a caregiver for the animal;
provide treatment modality information to the caregiver;
wherein the intelligent health monitoring device comprises: a housing comprising a casing member releasably couplable with a base member, wherein the casing member and the base member create an internal cavity when in a coupled configuration;
an environment resistant seal disposed between the casing member and the base member, wherein the environment resistant seal is held between the casing member and the base member when the casing member and the base member are in the coupled configuration;
a stud coupled to a side of the base member, the stud configured to pierce biological tissue;
wherein the processor, the memory, the power source, and the communications interface, are operatively coupled together and held within an internal cavity, at least two or more of which are separately releasable from within the internal cavity;
a conductor operatively coupled to the processor and a heat sensor, a portion of the conductor disposed within a flexible cord passing through an opening in the housing and extending outside the internal cavity to at least a portion of the heat sensor.

11. The intelligent health monitoring engine of claim 10, wherein the remote intelligent health monitoring device is attachable to an ear of the animal, and the temperature data is based on heat sensed within the ear canal of the animal.

12. The intelligent health monitoring engine of claim 10, wherein the health condition criteria comprises a temperature threshold.

13. The intelligent health monitoring engine of claim 10, wherein determining whether temperature data satisfies a health condition criteria is based upon one or more of an ambient temperature near a location of the animal, and a length of time during which the temperature data satisfied the health condition criteria.

14. The intelligent health monitoring engine of claim 10, wherein identifying a treatment modality to be delivered to the animal to treat a health condition is based on one or more of: a breed of the animal, an age of the animal, a size of the animal, a treatment history of the animal, and a known allergy of the animal.

15. The intelligent health monitoring engine of claim 10, wherein identifying a treatment modality to be delivered to the animal to treat a health condition is based on one or more of: an availability of the treatment modality, an effectiveness of the treatment modality, and a cost of the treatment modality.

16. The intelligent health monitoring engine of claim 10, wherein identifying a treatment modality to be delivered to the animal to treat a health condition comprises selecting among a plurality of medications to deliver to the animal.

17. The intelligent health monitoring engine of claim 10, wherein providing treatment modality information to the caregiver comprises: generating one or more of a text message, an email, or a phone call describing the treatment modality information.

18. The intelligent health monitoring engine of claim 10, wherein treatment modality information comprises one or more of: a medication type, availability, dosage, and delivery site.

19. An intelligent health monitoring engine comprising:
a processor;
a memory;
a power source;
a communications interface to receive data from a remote intelligent health monitoring device;
a non-transitory computer readable medium storing machine readable instructions that, when executed by the processor, cause the intelligent health monitoring engine to:
acquire physical parameter data associated with an animal based on one or more physical parameter measures obtained by remote intelligent health monitoring device;
determine whether the physical parameter data satisfies a health condition criteria;
identify a treatment modality to be delivered to the animal to treat a health condition if a health condition criteria has been satisfied;
identify a caregiver for the animal;
provide treatment modality information to the caregiver;
wherein the processor, the memory, the power source, and the communications interface, are operatively coupled together and held within an internal cavity, at least two or more of which are separately releasable from within the internal cavity.

20. The intelligent health monitoring engine of claim 10, wherein the remote intelligent health monitoring engine is attached to the ear of the animal, and the physical parameter data is based on heat sensed within the ear canal of the animal.

* * * * *